United States Patent
Kapoor et al.

(10) Patent No.: US 8,688,208 B2
(45) Date of Patent: Apr. 1, 2014

(54) METHOD AND SYSTEM FOR MESHING HUMAN AND COMPUTER COMPETENCIES FOR OBJECT CATEGORIZATION

(75) Inventors: Ashish Kapoor, Seattle, WA (US); Eric J. Horvitz, Kirkland, WA (US); Desney S. Tan, Kirkland, WA (US); Pradeep U. Shenoy, Seattle, WA (US)

(73) Assignee: Microsoft Corporation, Redmond, WA (US)

( * ) Notice: Subject to any disclaimer, the term of this patent is extended or adjusted under 35 U.S.C. 154(b) by 678 days.

(21) Appl. No.: 12/362,472

(22) Filed: Jan. 29, 2009

(65) Prior Publication Data
US 2009/0137924 A1 May 28, 2009

Related U.S. Application Data

(63) Continuation-in-part of application No. 11/845,583, filed on Aug. 27, 2007.

(51) Int. Cl.
*A61B 5/02* (2006.01)

(52) U.S. Cl.
USPC .................................................. 600/544

(58) Field of Classification Search
USPC ................................................ 600/544–545
See application file for complete search history.

(56) References Cited

U.S. PATENT DOCUMENTS

| | | | |
|---|---|---|---|
| 4,203,452 A | 5/1980 | Cohen | |
| 5,003,986 A | 4/1991 | Finitzo et al. | |
| 5,363,858 A | 11/1994 | Farwell | |
| 5,447,166 A | 9/1995 | Gevins | |
| 5,797,853 A | 8/1998 | Musha et al. | |
| 5,957,859 A | 9/1999 | Rosenfeld | |
| 6,665,560 B2 | 12/2003 | Becker et al. | |
| 6,829,502 B2 | 12/2004 | Hong et al. | |
| 7,120,486 B2 | 10/2006 | Leuthardt et al. | |
| 7,299,213 B2 | 11/2007 | Cristianini | |
| 7,949,186 B2 * | 5/2011 | Grauman et al. | 382/170 |
| 2001/0020137 A1 | 9/2001 | Granger | |

(Continued)

FOREIGN PATENT DOCUMENTS

| | | |
|---|---|---|
| GB | 2220089 A | 12/1989 |
| WO | WO0044279 A1 | 8/2000 |
| WO | WO0056211 A1 | 9/2000 |
| WO | WO2005018455 A1 | 3/2005 |

OTHER PUBLICATIONS

"Combining brain computer interfaces with vision for object categorization" by Ashish Kapoor, Pradeep Shenoy, Desney S. Tan, Computer Vision and Pattern Recognition Conference, 2008, pp. 1-8.*

(Continued)

*Primary Examiner* — Patricia Mallari
*Assistant Examiner* — Vasuda Ramachandran
(74) *Attorney, Agent, or Firm* — Lyon & Harr, LLP; Richard T. Lyon

(57) ABSTRACT

The subject disclosure relates to a method and system for visual object categorization. The method and system include receiving human inputs including data corresponding to passive human-brain responses to visualization of images. Computer inputs are also received which include data corresponding to outputs from a computerized vision-based processing of the images. The human and computer inputs are processing so as to yield a categorization for the images as a function of the human and computer inputs.

19 Claims, 26 Drawing Sheets

(56) References Cited

U.S. PATENT DOCUMENTS

| | | | |
|---|---|---|---|
| 2005/0017870 A1* | 1/2005 | Allison et al. | 340/825.19 |
| 2005/0043614 A1* | 2/2005 | Huizenga et al. | 600/427 |
| 2005/0181386 A1* | 8/2005 | Diamond et al. | 435/6 |
| 2007/0055169 A1 | 3/2007 | Lee et al. | |
| 2007/0217676 A1 | 9/2007 | Grauman et al. | |
| 2008/0010245 A1* | 1/2008 | Kim et al. | 707/2 |

OTHER PUBLICATIONS

Anderson et al, "SETI@home: An Experiment in Public-resource Computing", Communications of the Association of Computing Machines, Nov 2002, vol. 45, No. 11, pp. 56-61.

Cai, "Instinctive Computing", Book—Human Computing, 2007, pp. 17-46.

Gerson et al, "Cortically Coupled Computer Vision for Rapid Image Search", IEEE Trans. on Neural Systems nad Rehabilitation Engineering, Jun. 2006, vol. 14, No. 2, pp. 174-179.

Griffin et al, "The Caltech-256 Object Category Dataset", Caltech Technical Report, Mar. 2007, 20 pgs.

Grill-Spector, "The Neural Basis of Object Perception", Current Opinion in Neurobiology, Apr. 2003, vol. 13, pp. 1-8.

Hoffmann et al, "Spatial Filters for the Classification of Event-related Potentials", European Symposium on Artificial Neural Networks, Apr. 2006, pp. 47-52.

Itier et al, "N170 or N1? Spatiotemporal Differences Between Object and Face Processing using ERP's", Cerebral Cortex, Feb. 2006, vol. 14, pp. 132-142.

Johnson et al, "The Earliest EEG Signatures of Object Recognition in a Cued-target Task are Postsensory", J. of Vision, Apr. 2005, vol. 5, No. 4, pp. 299-312.

Kaplan et al, "The Conception of Intellectual Brain Computer Interface: Fundamentals and Experiment", 1st Indian Int. Conf. Artif. Intelligence, IICAI 2003, Dec. 2003, pp. 712-721.

Koch et al, "Attention and Consciousness: Two Distinct Brain Processes", Trends in Cognitive Sciences, Jan. 2007, vol. 11, No. 1, pp. 16-22.

Larson et al, "Folding@home and genome@home: Using Distributed Computing to Tackle Previously Intractable Problems in Computational Biology", Computational Genomics: Theory and Application, R. Grant (ed), 31 pgs.

Lee et al, "Using a Low-cost Electroencephalograph for Task Classification in HCI Research", Proc. of the 19th Annual ACM Symposium on User Interface Software and Tech., Oct. 2006, pp. 81-90.

Rossion et al, "Does the N170 Occipito-temporal Component Reflect a Face-specific Structural Encoding Stage?", OPAM 99, Nov. 1999, 11 pgs.

Velmans, "Is Human Information Processing Conscious?", Behavioral and Brain Sciences, 1991, vol. 14, pp. 651-726, Cambridge University Press.

von Ahn, "Games with a Purpose", IEEE Computer Magazine, Jun. 2006, vol. 39 , No. 6, 3 pgs.

von Ahn, "Labeling Images with a Computer Game", Proc. of the SIGCHI Conf. on Human Factors in Computing Sys., Apr. 2004, pp. 319-326.

von Ahn, L., R. Liu, M. Blum, Peekaboom: A game for locating objects in images, Proc. of the 2006 Conf. on Human Factors in Computing Sys's, CHI 2006, Apr. 22-27, 2006, pp. 55-64, Montréal, Québec, Canada.

Delorme, A., G. A. Rousselet, M. J.-M. Macé, M. Fabre-Thorpe, Interaction of top-down and bottom-up processing in the fast visual analysis of natural scenes, Cognitive Brain Research, Apr. 2004, pp. 103-113, vol. 19.

Bart, E., S. Ullman, Cross-generalization: Learning novel classes from a single example by feature replacement, 2005 IEEE Comp. Soc. Conf. on Comp. Vision and Pattern Recognition, Jun. 20-26, 2005, pp. 672-679, vol. 1, San Diego, CA, USA.

Bennett, P. N., S. T. Dumais, E. Horvitz, The combination of text classifiers using reliability indicators, Information Retrieval, Jan. 2005, pp. 67-100, vol. 8, No. 1.

Biosemi, Biosemi EEG ECG EMG BSPM Neuro amplifier electrodes, retrieved Oct. 6, 2008 from http://www.biosemi.com/, p. 1.

Blum, A., T. M. Mitchell, Combining labeled and unlabeled data with co-training, Proc. of the Eleventh Annual Conf. on Computational Learning Theory, COLT 1998, Jul. 24-26, 1998, pp. 92-100, Madison, Wisconsin, USA.

Breiman, L., Bagging predictors machine learning, Machine Learning, Aug. 1996, pp. 123-140, vol. 24, No. 2.

Chang, C.-C., and C.-J. Lin, LIBSVM—A Library for Support Vector Machines, retrieved Oct. 6, 2008 from http://www.csie.ntu.edu.tw/~cjlin/libsvm/, Pages 4.

Cristianini, N., J. Shawe-Taylor, A. Elisseeff, J. S. Kandola, on kernel-target alignment, Advances in Neural Information Processing Systems, Dec. 3-8, 2001, pp. 367-373, vol. 14, Vancouver, British Columbia, Canada.

Dasgupta, S., A. T. Kalai, C. Monteleoni, Analysis of perceptron-based active learning, Proceedings of the 18th Annual Conf on Learning Theory, COLT 2005, Jun. 27-30, 2005, pp. 249-263, Bertinoro, Italy.

Farwell, L. A., E. Donchin, Talking off the top of your head: Toward a mental prosthesis utilizing event-related brain potentials, Electroencephalography and Clinical Neurophysiology, Dec. 1988, pp. 510-523, vol. 70, No. 6.

Fei-Fei, L., R. Fergus, P. Perona, Learning generative visual models from few training examples: An incremental Bayesian approach tested on 101 object categories, Computer Vision and Image Understanding, Apr. 2007, pp. 59-70, vol. 106, No. 1.

Fergus, R., P. Perona, A. Zisserman, Object class recognition by unsupervised scale-invariant learning, IEEE Computer Society Conference on Computer Vision and Pattern Recognition, Jun. 16-22, 2003, pp. 264-271, vol. 2, Madison, WI, USA.

Grauman, K., T. Darrell, Approximate correspondences in high dimensions, Proc. of the Twentieth Annual Conference on Neural Information Processing Sys's, Dec. 4-7, 2006, pp. 505-512, vol. 19, Vancouver, British Columbia, Canada.

Grauman, K., T. Darrell, The pyramid match kernel: Discriminative classification with sets of image features, 10th IEEE Intl Conf. on Computer Vision, Oct. 17-20, 2005, pp. 1458-1465, Beijing, China.

Ivanov, Y., T. Serre, J. Bouvrie, Error weighted classifier combination for multimodal human identification, Computer Science and Artificial Intelligence Laboratory, Technical Report, MIT-CSAIL-TR-2005-081, Dec. 14, 2005, Pages 7.

Kapoor, A., K. Grauman, R. Urtasun, T. Darrell, Active learning with Gaussian processes for object categorization, IEEE 11th Int'l Conf. on Comp. Vision, ICCV 2007, Oct. 14-20, 2007, pp. 1-8, Rio de Janeiro, Brazil.

Kapoor, A., P. Shenoy, D. S. Tan, Combining brain computer interfaces with vision for object categorization, IEEE Comp. Soc. Conf. On Comp. Vision and Pattern Recognition, CVPR 2008, Jun. 24-26, 2008, Pages 8, Anchorage, Alaska, USA.

Kittler, J., M. Hatef, R. P.W. Diun, and J. Matas, On combining classifiers, IEEE Transactions on Pattern Analysis and Machine Intelligence, Mar. 1998, pp. 226-239, vol. 20, No. 3.

Krause, A., A. P. Singh, C. Guestrin, Near-optimal sensor placements in Gaussian processes: Theory, efficient algorithms and empirical studies, J. of Machine Learning Research, Feb. 2008, pp. 235-284, vol. 9.

Lanckriet, G. R. G., N. Cristianini, P. L. Bartlett, L. E. Ghaoui, M. I. Jordan, Learning the kernel matrix with semidefinite programming, J. of Machine Learning Research, Jan. 2004, pp. 27-72, vol. 5.

Lazebnik, S., C. Schmid, J. Ponce, Beyond bags of features: Spatial pyramid matching for recognizing natural scene categories, IEEE Computer Society Conference on Computer Vision and Pattern Recognition, pp. 2169-2178, Jun. 17-22, 2006, New York, NY, USA.

Lee, J. J., Libpmk: A pyramid match toolkit, Tech Report MIT-CSAIL-TR-2008-17, Apr. 2008, http://people.csail.mit.edu/jjl/libpmk/, Pages 3.

Leuthardt, E. C., G. Schalk, J. R. Wolpaw, J. G. Ojemann, D. W. Moran, A brain-computer interface using electrocorticographic signals in humans, J. Neural Eng. Jun. 14, 2004, pp. 63-71, vol. 1, No. 2.

(56) References Cited

OTHER PUBLICATIONS

Li, Y., C. Guan, H. Li, Z. Chin, A self-training semi-supervised SVM algorithm and its application in an EEG-based brain computer interface speller system, Pattern Recognition Letters, Jul. 2008, pp. 1285-1294, vol. 29, No. 9.
Lowe, D. G., Distinctive image features from scale-invariant keypoints, Int'l J. of Computer Vision, Jan. 5, 2004, pp. 91-110, vol. 60, No. 2.
MacKay, D. J. C., Information-based objective functions for active data selection, Neural Computation, Jul. 1992, pp. 590-604, vol. 4, No. 4.
Mikolajczyk, K., C. Schmid, Indexing based on scale invariant interest points, Proc. Eighth IEEE Intl Conf. on Comp. Vision, ICCV 2001, Jul. 7-14, 2001, pp. 525-531, vol. 1.
Miller, D. J., L. Yan, Critic-driven ensemble classification, IEEE Transactions on Signal Proc., Oct. 1999, pp. 2833-2844, vol. 47, No. 10.
Moosmann, F., B. Triggs, F. Jurie, Fast discriminative visual codebooks using randomized clustering forests, Proc. of the Twentieth Annual Conf. on Neural Info. Processing Systems, NIPS 2006, Dec. 4-7, 2006, pp. 985-992, vol. 19, Vancouver, British Columbia, Canada, MIT Press 2007.
Muslea, I., S. Minton, C. A. Knoblock, Active learning with multiple views, J. of Artificial Intelligence Research, Sep. 2006, pp. 203-233, vol. 27, No. 1.
Nistér, D., H. Stewenius, Scalable recognition with a vocabulary tree, 2006 IEEE Comp. Society Conf. on Comp. Vision and Pattern Recognition, CVPR 2006, Jun. 17-22, 2006, pp. 2161-2168, vol. 2, New York, NY, USA.
Noort, M. van den, K. Hugdahl, P. Bosch, Human machine interaction: The special role for human unconscious emotional information processing, ACII 2005 Proc. of the First Intl Conf. on Affective Computing and Intelligent Interaction, Oct. 22-24, 2005, pp. 598-605, Beijing, China.
Oliver, N., A. Garg, E. Horvitz, Layered representations for learning and inferring office activity from multiple sensory channels, Computer Vision and Image Understanding, Nov. 2004, pp. 163-180, vol. 96, No. 2.
Platt, J. C., C. J. C. Burges, S. Swenson, C. Weare, a. Zheng, Learning a Gaussian process prior for automatically generating music playlists, Advances in Neural Information Processing Systems, Neural Information Processing Systems: Natural and Synthetic, NIPS 2001, Dec. 3-8, 2001, pp. 1425-1432, vol. 14, Vancouver, British Columbia, Canada.
Russell, B., A. Torralba, W. T. Freeman, LabelMe: The open annotation tool, retrieved Oct. 7, 2008 from http://labelme.csail.mit.edu/, Page 1.
Schapire, R. E., A brief introduction to boosting, Proc. of the Sixteenth Int'l Joint Conf. on Artificial Intelligence, Jul. 31-Aug. 6, 1999, pp. 1401-1406, Stockholm, Sweden.
Schyns, P. G., L. S. Petro, M. L. Smith, Dynamics of visual information integration in the brain for categorizing facial expressions, Current Biology, Sep. 18, 2007, pp. 1580-1585, vol. 17.
Shenoy, P., D. S. Tan, Human-aided computing: Utilizing implicit human processing to classify images, Proc. of the 2008 Conf. on Human Factors in Computing Sys's, CHI 2008, Apr. 5-10, 2008, pp. 845-854, Florence, Italy.
Sivic, J., A. Zisserman, Video Google: Efficient visual search of videos. Toward category-level object recognition, Proc. of the Ninth IEEE Int'l Conf. on Comp. Vision, ICCV 2003, Oct. 13-16, 2003, pp. 1470-1477, vol. 2, Nice, France.
Tong, S., D. Koller, Active learning for parameter estimation in Bayesian networks, Advances in Neural Info. Processing Sys's, NIPS 2000, Nov. 27-Dec. 2, 2000, pp. 647-653, vol. 13, Denver, CO, USA.
Toyama, K., E. Horvitz, Bayesian modality fusion: Probabilistic integration of multiple vision algorithms for head tracking, Fourth Asian Conf. on Comp. Vision, ACCV 2000, Jan. 2000, pp. 8, Taipei, Taiwan.
Varma, M., D. Ray, Learning the discriminative power-invariance trade-off, ICCV 2007, IEEE 11th Int'l Conf. on Comp. Vision, ICCV 2007, Oct. 14-20, 2007, pp. 1-8, Rio de Janeiro, Brazil.
Wallraven, C., B. Caputo, A. B. A. Graf, Recognition with local features: The kernel recipe, 9th IEEE Intl Conf. on Comp. Vision, ICCV 2003, Oct. 14-17, 2003, pp. 257-264, Nice, France.
Wang, W., Z.-H. Zhou, On multi-view active learning and the combination with semi-supervised learning, Proc. of the Twenty-Fifth Int'l Conf. on Machine Learning, ICML 2008, Jun. 5-9, 2008, pp. 1152-1159, Helsinki, Finland.
Yu, S., B. Krishnapuram, R. Rosales, H. Steck, R. B. Rao, Bayesian co-training, Proc. of the Twenty-First Annual Conf. on Neural Info. Processing Sys's, Advances in Neural Info. Processing Sys's, NIPS 2007, Dec. 3-6, 2007, pp. 1-8, vol. 20, Vancouver, British Columbia, Canada.
Zhang, J., M. Marszalek, S. Lazebnik, C. Schimid, Local features and kernels for classification of texture and object categories: A comprehensive study, Int'l J. of Comp. Vision, Jun. 2007, pp. 213-238, vol. 73, No. 2.
Zhang, H., A. C. Berg, M. Maire, J. Malik, SVM-KNN: Discriminative nearest neighbor classification for visual category recognition, IEEE Computer Society Conference on Computer Vision and Pattern Recognition, CVPR 2006, Jun. 17-22, 2006, pp. 2126-2136, vol. 2, New York, NY, USA.
Ramachandran, V., Final Office Action, U.S. Appl. No. 11/845,583, Aug. 1, 2013, pp. 26.
Ramachandran, V., U.S. Office Action, U.S. Appl. No. 11/845,583, Nov. 21, 2013, pp. 1-29.

* cited by examiner $$K_\Delta = \begin{pmatrix} K_{\Delta 11} & K_{\Delta 12} & K_{\Delta 13} \cdots K_{\Delta 1n} \\ K_{\Delta 12} & K_{\Delta 22} & K_{\Delta 23} \cdots K_{\Delta 2n} \\ K_{\Delta 13} & K_{\Delta 23} & K_{\Delta 33} \cdots K_{\Delta 3n} \\ \vdots & \vdots & \vdots \ddots \vdots \\ K_{\Delta 1n} & K_{\Delta 2n} & K_{\Delta 3n} \cdots K_{\Delta nn} \end{pmatrix}$$

COMPUTER PROCESSED SIMILARITY MATRIX (n IMAGES)

FIG. 3

$$K_\xi = \begin{Vmatrix} K_{\xi 11} & K_{\xi 12} & K_{\xi 13} & \cdots & K_{\xi 1n} \\ K_{\xi 12} & K_{\xi 22} & K_{\xi 23} & \cdots & K_{\xi 2n} \\ K_{\xi 13} & K_{\xi 23} & K_{\xi 33} & \cdots & K_{\xi 3n} \\ \vdots & \vdots & \vdots & \ddots & \vdots \\ K_{\xi 1n} & K_{\xi 2n} & K_{\xi 3n} & \cdots & K_{\xi nn} \end{Vmatrix}$$

HUMAN PROCESSED SIMILARITY MATRIX ($n$ IMAGES)

FIG. 6

$$K = \begin{bmatrix} K_{11} & K_{12} & K_{13} & \cdots & K_{1n} \\ K_{12} & K_{22} & K_{23} & \cdots & K_{2n} \\ K_{13} & K_{23} & K_{33} & \cdots & K_{3n} \\ \vdots & \vdots & \vdots & \ddots & \vdots \\ K_{1n} & K_{2n} & K_{3n} & \cdots & K_{nn} \end{bmatrix}$$

K = FUSED HUMAN/COMPUTER PROCESSED SIMILARITY MATRIX (*n* IMAGES)

$$K^{(j)} = \begin{pmatrix} K^{(j)}_{11} & K^{(j)}_{12} & K^{(j)}_{13} & \cdots & K^{(j)}_{1n} \\ K^{(j)}_{12} & K^{(j)}_{22} & K^{(j)}_{23} & \cdots & K^{(j)}_{2n} \\ K^{(j)}_{13} & K^{(j)}_{23} & K^{(j)}_{33} & \cdots & K^{(j)}_{3n} \\ \vdots & \vdots & \vdots & \ddots & \vdots \\ K^{(j)}_{1n} & K^{(j)}_{2n} & K^{(j)}_{3n} & \cdots & K^{(j)}_{nn} \end{pmatrix}$$

SINGLE VIEW SIMILARITY MATRIX ($n$ IMAGES)

FIG. 17

$$K^{(C)} = \begin{pmatrix} K^{(C)}_{11} & K^{(C)}_{12} & K^{(C)}_{13} & \cdots & K^{(C)}_{1n} \\ K^{(C)}_{12} & K^{(C)}_{22} & K^{(C)}_{23} & \cdots & K^{(C)}_{2n} \\ K^{(C)}_{13} & K^{(C)}_{23} & K^{(C)}_{33} & \cdots & K^{(C)}_{3n} \\ \vdots & \vdots & \vdots & \ddots & \vdots \\ K^{(C)}_{1n} & K^{(C)}_{2n} & K^{(C)}_{3n} & \cdots & K^{(C)}_{nn} \end{pmatrix}$$

MULTI-VIEW CONSENSUS SIMILARITY MATRIX ($n$ IMAGES)

FIG. 18

$$\mathbf{K}^{(a)} = \begin{array}{|cccccc|} \hline K^{(a)}_{11} & K^{(a)}_{12} & K^{(a)}_{13} & \cdots & & K^{(a)}_{1n} \\ K^{(a)}_{12} & K^{(a)}_{22} & K^{(a)}_{23} & \cdots & & K^{(a)}_{2n} \\ K^{(a)}_{13} & K^{(a)}_{23} & K^{(a)}_{33} & \cdots & & K^{(a)}_{3n} \\ \vdots & & & \ddots & & \vdots \\ K^{(a)}_{1n} & K^{(a)}_{2n} & K^{(a)}_{3n} & \cdots & & K^{(a)}_{nn} \\ \hline \end{array}$$

(complete "a" view of images 1 through n)

$$\mathbf{K}^{(b)} = \begin{array}{|cccccc|} \hline K^{(b)}_{11} & \text{missing} & K^{(b)}_{13} & \cdots & & K^{(b)}_{1n} \\ \text{missing} & \text{missing} & \text{missing} & \cdots & & \text{missing} \\ K^{(b)}_{13} & \text{missing} & K^{(b)}_{33} & \cdots & & K^{(b)}_{3n} \\ \vdots & & & \ddots & & \vdots \\ K^{(b)}_{1n} & \text{missing} & K^{(b)}_{3n} & \cdots & & K^{(b)}_{nn} \\ \hline \end{array}$$

(missing "b" view of image 2)

$$\mathbf{K}^{(c)} = \begin{array}{|cccccc|} \hline K^{(c)}_{11} & K^{(c)}_{12} & \text{missing} & \cdots & & K^{(c)}_{1n} \\ K^{(c)}_{12} & K^{(c)}_{22} & \text{missing} & \cdots & & K^{(c)}_{2n} \\ \text{missing} & \text{missing} & \text{missing} & \cdots & & \text{missing} \\ \vdots & & & \ddots & & \vdots \\ K^{(c)}_{1n} & K^{(c)}_{2n} & \text{missing} & \cdots & & K^{(c)}_{nn} \\ \hline \end{array}$$

(missing "c" view of image 3)

$$K^{(a)} = \begin{vmatrix} K^{(a)}_{11} & K^{(a)}_{12} & K^{(a)}_{13} & \cdots & K^{(a)}_{1n} \\ K^{(a)}_{12} & K^{(a)}_{22} & K^{(a)}_{23} & \cdots & K^{(a)}_{2n} \\ K^{(a)}_{13} & K^{(a)}_{23} & K^{(a)}_{33} & \cdots & K^{(a)}_{3n} \\ \vdots & \vdots & \vdots & \ddots & \vdots \\ K^{(a)}_{1n} & K^{(a)}_{2n} & K^{(a)}_{3n} & \cdots & K^{(a)}_{nn} \end{vmatrix}$$

(complete "a" view of images 1 through $n$)

$$K^{(b)} = \begin{vmatrix} K^{(b)}_{11} & K^{(b)}_{proxy} & K^{(b)}_{13} & \cdots & K^{(b)}_{1n} \\ K^{(b)}_{proxy} & K^{(b)}_{proxy} & K^{(b)}_{proxy} & \cdots & K^{(b)}_{proxy} \\ K^{(b)}_{13} & K^{(b)}_{proxy} & K^{(b)}_{33} & \cdots & K^{(b)}_{3n} \\ \vdots & \vdots & \vdots & \ddots & \vdots \\ K^{(b)}_{1n} & K^{(b)}_{proxy} & K^{(b)}_{3n} & \cdots & K^{(b)}_{nn} \end{vmatrix}$$

(proxy "b" view of image 2)

$$K^{(c)} = \begin{vmatrix} K^{(c)}_{11} & K^{(c)}_{12} & K^{(c)}_{proxy} & \cdots & K^{(c)}_{1n} \\ K^{(c)}_{12} & K^{(c)}_{22} & K^{(c)}_{proxy} & \cdots & K^{(c)}_{2n} \\ K^{(c)}_{proxy} & K^{(c)}_{proxy} & K^{(c)}_{proxy} & \cdots & K^{(c)}_{proxy} \\ \vdots & \vdots & \vdots & \ddots & \vdots \\ K^{(c)}_{1n} & K^{(c)}_{2n} & K^{(c)}_{proxy} & \cdots & K^{(c)}_{nn} \end{vmatrix}$$

(proxy "c" view of image 3)

METHOD AND SYSTEM FOR MESHING HUMAN AND COMPUTER COMPETENCIES FOR OBJECT CATEGORIZATION

CROSS-REFERENCE TO RELATED APPLICATION

This application is a continuation-in-part of pending U.S. patent application Ser. No. 11/845,583 entitled "CATEGORIZING PERCEPTUAL STIMULI BY DETECTING SUBCONCIOUS RESPONSES" and filed on Aug. 27, 2007. The entirety of the above-referenced application is incorporated by reference herein.

TECHNICAL FIELD

The subject disclosure generally relates to categorizing objects in an image, and more particularly towards a method and system for categorizing objects that fuses computer vision-based processing with processing executed by a human brain.

BACKGROUND

Recent research has sought to develop principles and applications of human-aided and, more generally, mixed-initiative problem solving, where complementary contributions from people and computing systems are combined to generate solutions. The ideal mix of human and computer contributions changes as the competencies of computational systems grow and with the development of new ways for people and machines to collaborate, with sequential or parallel efforts. People are known to perform better than the best available computational algorithms for high-level reasoning, decision making, and recognition, especially when these tasks rely on a deep fund of commonsense knowledge.

Visual category recognition is a particularly challenging problem and techniques based on computer vision often require human involvement to learn good object category models. The most basic level of human involvement is providing labeled data that the system can use to learn visual categories. Since this labeling process is often very expensive, much recent work has focused on ways to reduce the number of labeled examples required to learn accurate models. These systems aim to maximally utilize the human effort involved in labeling examples. Other solutions for addressing the labeling problem include embedding the labeling task in popular games, and asking users to provide finer-grained information by selecting and labeling specific objects within images. Implementing such a method, however, is costly and still requires active participation from a user.

Accordingly, there is a need for an efficient visual object categorization framework that fuses and identifies the respective strengths of computer and human processing, while minimizing the amount of human involvement required. The above-described deficiencies of current techniques are merely intended to provide an overview of some of the problems of conventional systems, and are not intended to be exhaustive. Other problems with conventional systems and corresponding benefits of the various non-limiting embodiments described herein may become further apparent upon review of the following description.

SUMMARY

A simplified summary is provided herein to help enable a basic or general understanding of various aspects of exemplary, non-limiting embodiments that follow in the more detailed description and the accompanying drawings. This summary is not intended, however, as an extensive or exhaustive overview. Instead, the sole purpose of this summary is to present some concepts related to some exemplary non-limiting embodiments in a simplified form as a prelude to the more detailed description of the various embodiments that follow.

Embodiments of a method and system for human-aided object categorization are described. In various non-limiting embodiments, the method and system include fusing computer vision-based processing and processing done by the human brain in order to build more effective object categorization systems. In an embodiment, an electroencephalograph (EEG) device is utilized to measure the subconscious cognitive processing that occurs in the brain as users see images, even when they are not trying to explicitly classify them. A novel framework is provided that combines a discriminative visual category recognition system with information derived from EEG measurements as users view images. In one aspect, a fast convex kernel alignment algorithm is implemented to combine the two sources of information. The effectiveness of various aspects of the disclosed method and system is validated with experiments using real-world data, where significant gains in classification accuracy are provided. Various properties of exemplary embodiments of the fused information are also analyzed by examining the relative contributions of the modalities, the errors arising from each source, and the stability of the combination in repeated experiments.

In another non-limiting embodiment, a method and system is provided for combining the efforts and competencies of human and machine computation using multi-view learning. Within such embodiment, human and computer competencies are relied upon for pattern classification when either of the computational sources is missing. An extension of a co-training model is disclosed to classify data with incomplete information, as well as to selectively sample information to determine the next best piece of information to seek, either from a human or a machine, to improve accuracy and maximize utility. Results highlighting the effectiveness of the proposed scheme in training image categorization models are also provided.

These and other embodiments are described in more detail below.

BRIEF DESCRIPTION OF THE DRAWINGS

Various non-limiting embodiments are further described with reference to the accompanying drawings in which:

FIG. 3 is an exemplary computer-processed similarity matrix in accordance with an aspect of the disclosed subject matter.

FIG. 6 is an exemplary human-processed similarity matrix in accordance with an aspect of the disclosed subject matter.

FIG. 7 is an exemplary fused similarity matrix in accordance with an aspect of the disclosed subject matter.

FIG. 13 is an illustration of exemplary errors resulting from experiments performed in accordance with an aspect of the disclosed subject matter.

FIG. 17 is an exemplary single-view similarity matrix in accordance with an aspect of the disclosed subject matter.

FIG. 18 is an exemplary multi-view consensus similarity matrix in accordance with an aspect of the disclosed subject matter.

FIG. 19 is an illustration of a complete single-view similarity matrix and two incomplete single-view similarity matrices in accordance with an aspect of the disclosed subject matter.

FIG. 20 is an illustration of a complete single-view similarity matrix and two proxy-filled single-view similarity matrices in accordance with an aspect of the disclosed subject matter.

DETAILED DESCRIPTION

Figure 1:
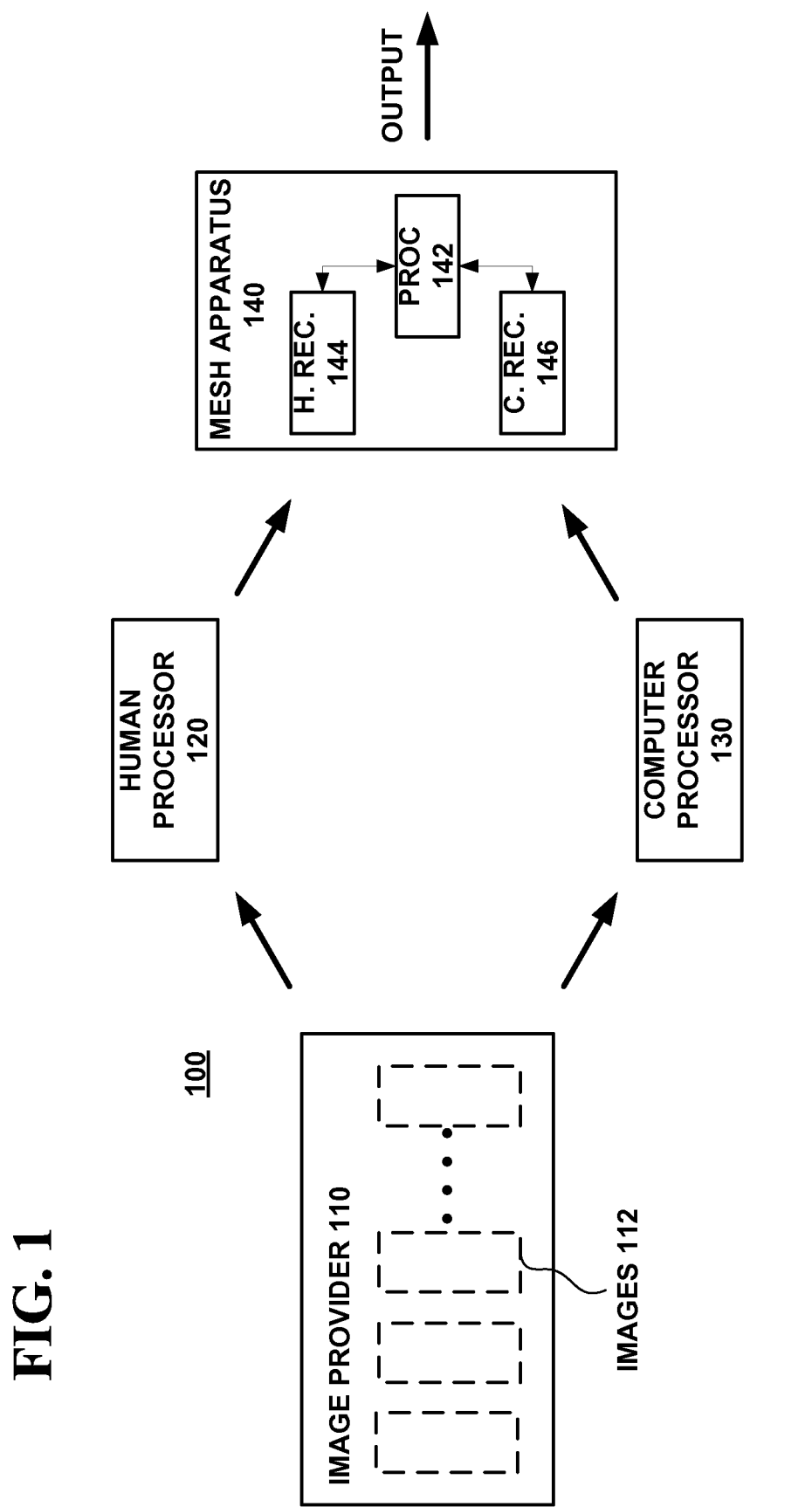
FIG. 1 is a non-limiting block diagram illustrating an exemplary system for fusing human processing with computer processing in accordance with an aspect of the disclosed subject matter.

The subject innovation is now described with reference to the drawings, wherein like reference numerals are used to refer to like elements throughout. In the following description, for purposes of explanation, numerous specific details are set forth in order to provide a thorough understanding of the disclosed subject matter. It may be evident, however, that the disclosed subject matter may be practiced without these specific details. In other instances, well-known structures and devices are shown in block diagram form in order to facilitate describing the various aspects.

Overview

Several non-limiting exemplary embodiments are now described. In one such embodiment, a novel form of human-aided computing is disclosed in which a user's brain signals are directly measured with little conscious effort from the user. This approach partially relies on a discovery that the human brain subconsciously processes different images in different ways measurable by certain brain-sensing technologies, even when the user is not trying to categorize images. By fusing these passive human responses with traditional computer vision-based techniques, several desirable synergies for object categorization are achieved which may be advantageously exploited.

For instance, by observing how human brain processes help boost traditional vision-based methods, insight is gained into aspects of images and categories that are not currently modeled by computer vision algorithms. This insight can then be utilized to build systems that match the robustness and flexibility of a human visual system.

It should also be noted that gathering labels via explicit human involvement for building visual categorization systems is an expensive and time-consuming process. However, by exploiting the implicit processing in the human brain to rapid presentation of images, the speed of the labeling process may be significantly increased and the need for collecting actual human-labeled training data may be significantly reduced.

Furthermore, since computers process images differently from human brains, the two modalities provide complementary information which may utilized to design more effective classifiers. For instance, whereas computer-based techniques generally focus on various imaging transformations, intra-class variations, and are often motivated by the specific vision-centric tasks, human-processing tends to be fairly task-invariant and shows characteristic responses that are more likely due to contextual or semantic associations.

In FIG. 1 a block diagram illustrating an exemplary system for fusing human processing with computer vision-based processing in accordance with an aspect of the disclosed subject matter is provided. As illustrated, exemplary system 100 includes image provider 110, human processor 120, computer vision-based processor 130, and mesh apparatus 140. Within such embodiment, image provider 110 provides a plurality of images 112 to each of human processor 120 and computer processor 130, either serially or in parallel. Once received, each of human processor 120 and computer processor 130 separately process plurality of images 112 so as to respectively generate a set of human-processed data and a set of computer-processed data. Each of the human-processed and computer-processed data are then input to mesh apparatus 140 for further processing according to a fusion algorithm.

In an embodiment, mesh apparatus 140 is a computing device that includes processor 142 coupled to each of receiving apparatus 144 and receiving apparatus 146, as shown. In one aspect, receiving component 144 is configured to receive at least one human input that includes data corresponding to a plurality of passive human-brain responses to visualization of plurality of images 112. Here, although only one human processor 120 is illustrated, it should be appreciated that human processor 120 may represent any number of human subjects providing a plurality of human inputs to mesh apparatus 140. It should be further noted that, although the disclosed subject matter describes EEGs as an exemplary human input, one of ordinary skill in the art would appreciate that any of various types/combinations of passive human-brain responses to visualization of images 112 may be similarly used.

In another aspect, receiving component 146 is configured to receive at least one computer input from computer processor 130. Within such embodiment, the received computer input includes data corresponding to a plurality of outputs from a computerized vision-based processing of plurality of images 112. Here, although only one computer processor 130 is illustrated, it should again be appreciated that computer processor 130 may represent any number of computer-processing apparatuses providing a plurality of computer inputs to mesh apparatus 140. It should be further noted that, although the disclosed subject matter describes Pyramid Match Kernel (PMK) values as an exemplary computer input, one of ordinary skill in the art would appreciate that any of various types/combinations of outputs from a computerized vision-based processing of images 112 may be similarly used.

In another aspect, processor 142 is configured to execute a fusing algorithm that generates an output as a function of each of the at least one human input and the at least one computer input. In an embodiment, such processing yields a categorization for at least one of plurality of images 112. In another embodiment, such processing yields a predictive model that relies upon human and computer competencies for subsequent classifications when either of the computational sources is missing. In yet another embodiment, such processing yields a co-training model to classify data with incomplete information, as well as to selectively sample subsequent information to improve accuracy of predictive models and maximize utility.

Figure 2:
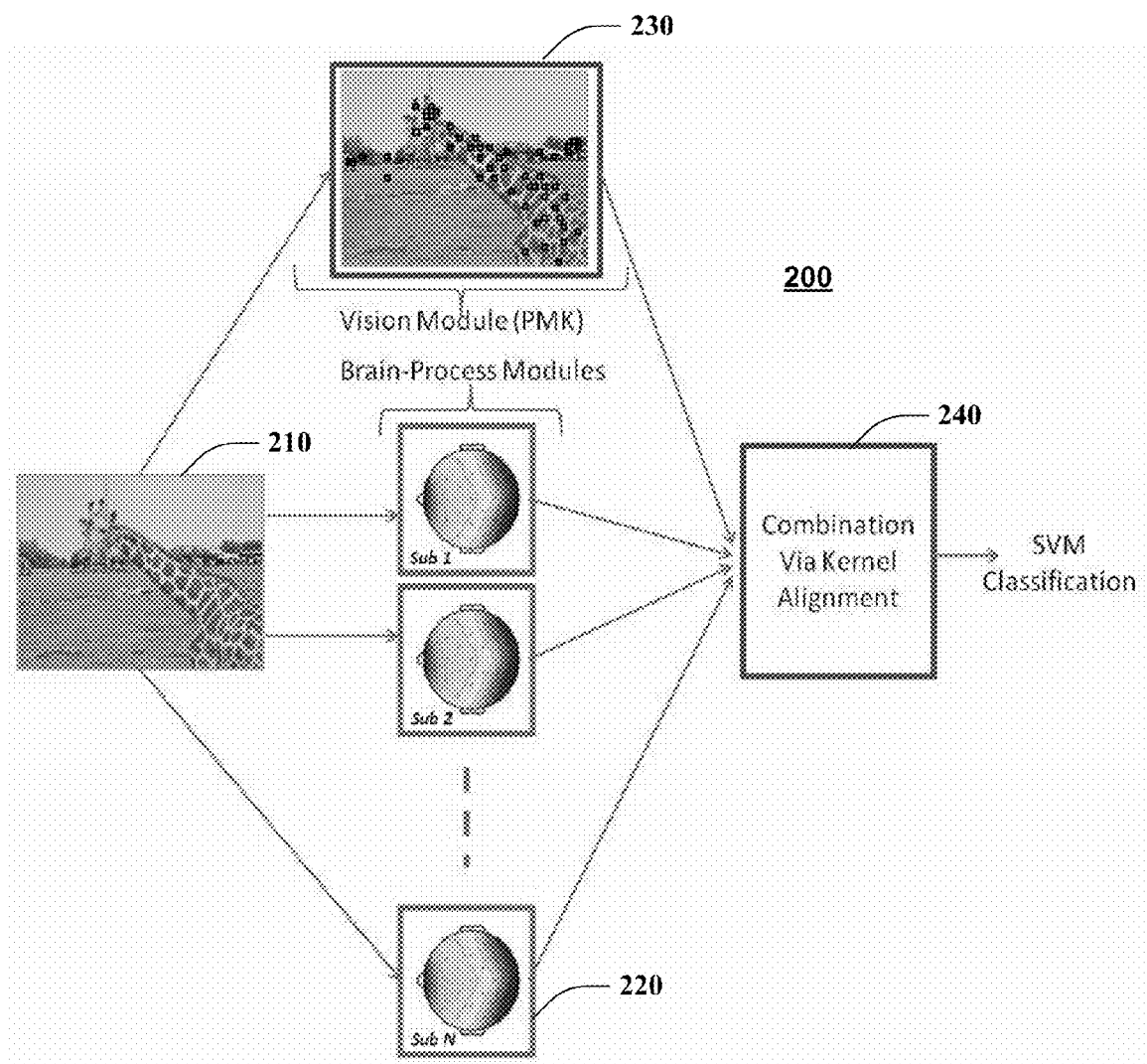
FIG. 2 is an exemplary framework for fusing EEGs with PMK values via Kernel alignment in accordance with an aspect of the disclosed subject matter.

Referring next to FIG. 2, an exemplary framework for fusing EEGs with PMK values via Kernel alignment is provided in accordance with a particular embodiment. Within such framework 200, the computer vision component 230 processes images 210 based on a PMK, which is a local feature correspondence kernel for object categorization. Object recognition based on local features has been shown to have several important advantages, including invariance to various translational, rotational, affine and photometric transformations and robustness to partial occlusions.

The human vision component of framework 200 is brain-process module 220 that measures EEG data from single or multiple users. Module 220 complements the computer-identified visual features with activations in a human brain as images 210 are presented to multiple subjects.

Framework 200 further includes fusion apparatus 240, which combines the human and computer modalities using a fast convex kernel alignment criterion. Within such embodiment, fusion apparatus 240 utilizes this combination to learn visual category models that are superior to the ones trained on only one of the modules.

Object Categorization with PMK

For this particular embodiment, although any of several computer vision-based processing methods can be utilized, a PMK method is used. By using a PMK, various vision-based similarities between images may be expressed in terms of partial match correspondences. The PMK method also provides an efficient linear-time approximation of the optimal partial-match correspondence.

Sets of local features provide a useful image representation for object categorization, as they often show tolerance to partial occlusions, object pose variation, and illumination changes. Generally an image is decomposed into local regions or patches, possibly according to an interest operator, and then a local descriptor is extracted to describe the shape or appearance of these patches. The matching or correspondence between two such sets can often reveal their overall similarity and localize highly distinctive object features. Several specialized set-correspondence kernels, however, may be used to exploit this object recognition property.

The PMK approximates the partial match similarity between sets of unordered feature vectors. Given a set of feature vectors, $S=\{s_1, \ldots, s_{|S|}\}$ where all $s_i \in \Re^d$, an L-level multi-resolution histogram $\Psi(S)=[H_0(S), \ldots, H_{L-1}(S)]$ is computed. This pyramid bins the features in such a way that an implicit hierarchical matching between $S_1$ and another set $S_2$ can be read off in time linear in $\max(|S_1|, |S_2|)$. The PMK value between two input sets $S_1$ and $S_2$ is defined as the weighted sum of the number of feature matches found at each level of their pyramids:

$$K_\Delta(\Psi(S_1), \Psi(S_2)) = \sum_{i=0}^{L-1} w_i (I(H_i(S_1), (H_i(S_2)) - I(H_{i-1}(S_1), (H_{i-1}(S_2))))$$

where I denotes histogram intersection, and the difference in intersections across levels serves to count the number of new matches formed at level i, which were not already counted at any finer resolution level. The weights are set to be inversely proportional to the size of the bins, in order to reflect the maximal distance two matched points could be from one another. As long as $w_i \geq w_{i+1}$, the kernel is Mercer.

The matching is partial in that some features may not have good matches but are not penalized in the matching score, and thus some clutter and background features is tolerated. The linear-time PMK offers a computationally appealing alternative to a cubic-time optimal matching method. This is useful in object recognition applications since densely sampled local features often yield better accuracy on category-level recognition problems. In addition, since PMK is a Mercer kernel, an SVM can be trained based on a pool of labeled images using $K_\Delta$, thus using the unordered sets of interest points in each image to determine visual similarity between images.

In FIG. 3, an exemplary PMK similarity matrix $K_\Delta$ is provided. For this particular example, a plurality of n images are processed by a computer vision-based system such that similarity matrix $K_\Delta$ is populated by individual PMK values $K_{\Delta ij}$. Moreover, each PMK value $K_{\Delta ij}$ is a similarity representation between images i and j.

Brain Computer Interface

Figure 4:
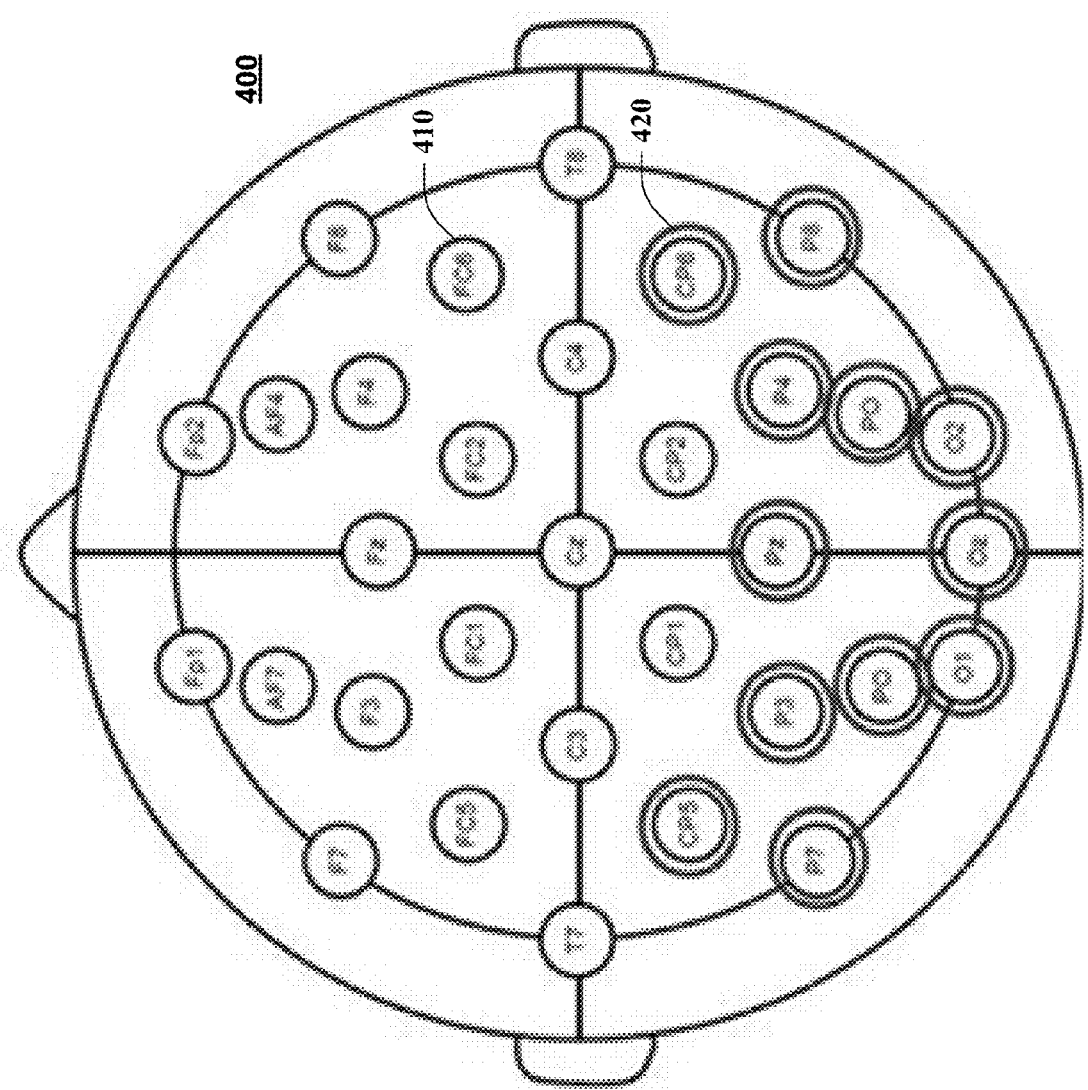
FIG. 4 is an exemplary layout for electrode placement in an electrode EEG measurement system in accordance with an aspect of the disclosed subject matter.

In an embodiment, an EEG device is used to observe cognitive activity as various images are presented to a human subject. An EEG is a neurophysiological measurement of brain activity using electrodes placed on the surface of the scalp. In FIG. 4, an exemplary layout for electrode placement in a 32-electrode EEG measurement system utilized in experiments performed in accordance with an aspect of the disclosed subject matter is provided.

Researchers often examine behavioral correlates in EEG signals by measuring the event-related potential (ERP), which represents the spatiotemporal shape of brain measurements in response to a discrete stimulus. By averaging this response across multiple presentations of stimuli and multiple subjects, researchers can learn about aggregate differences in responses between different classes of stimuli. For instance, the presentation of a human face is commonly connected with a pronounced negative drop in signal amplitude in certain channels approximately 170 ms following stimulus presentation.

Figure 5:
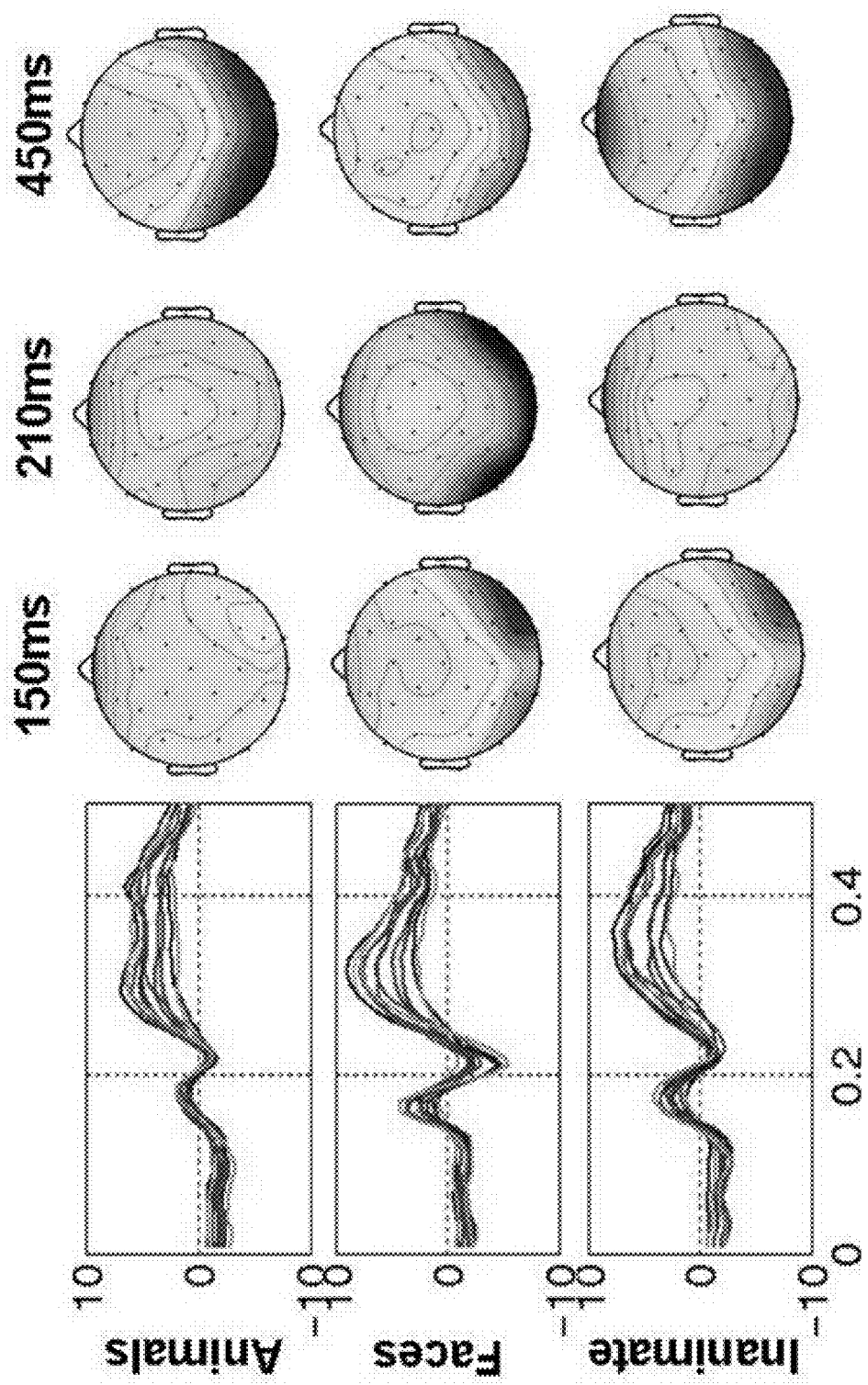
FIG. 5 is a set of graphs illustrating EEG responses and spatial distributions resulting from experiments performed in accordance with an aspect of the disclosed subject matter.

FIG. 5, for example depicts brain responses as images with three different labels are shown to human subjects. In FIG. 5, responses are averaged across multiple image presentations and each line represents the measurement of one of the channels from the EEG device in the first 0.5 s following stimulus presentation. For visualization purposes, scalp maps of the electrode readings for three time points are shown, highlighting the spatiotemporal difference in the EEG response to each category of images. It should be noted that the responses are significantly different for the three categories and there is enough discriminatory signal to train a classifier, indicating the discriminative power that may exist in this signal.

Related to this research is the study of brain-computer interfaces (BCI), which aims to allow users to communicate with the external world using brain signals alone. Many BCIs are based on a "recognition response" called a P300 that is evoked by stimuli of interest to the user. By detecting which of a series of stimuli (e.g., images, menu options, letters) generate this response, such systems can decode the user's intent or attention, and establish a communication channel such as a spelling device.

This P300 response has been exploited in previous systems including a system in which a user intentionally performs a visual search on a sequence of rapidly presented images, looking for a designated target image. Such a system can detect target images using the brain response alone, in certain cases faster than possible by manual identification using button presses. This system requires the user's explicit intent in searching for a single target or category of targets, and is a "target detector" system, rather than a detector for a specific category of objects. Therefore, such systems did not use computer vision algorithms to enhance EEG-based results.

In an embodiment, a novel complementary system for human-aided computing is utilized, in which the user is passively viewing images while performing a distracter task that does not consist of explicitly labeling or recognizing the images. Within such embodiment, the distracter task serves only to capture visual attention and cognitive processing. Experiments performed in accordance with aspects of the disclosed subject matter have shown that such passive EEG responses can be used to label images with at least one of three category labels, namely human faces, animals, and inanimate objects, with average accuracy of 55.3% using only a single presentation of an image. These experiments have further showed that the accuracy could be boosted by using multiple presentations to one or multiple users. With up to 10 presentations, the average labeling accuracy was raised to 73.5%. This system demonstrates that EEG signals could in principle be used as a new modality for extracting features from images for use in an object recognition system.

The disclosed subject matter extends this principle and explores a method for combining the information from EEG responses with state-of-the-art vision algorithms for object recognition. In several embodiments, vision algorithms based on correspondence kernels with local features are used in which a significant gain is obtained by incorporating EEG information. This suggests that there exists a set of complementary features in EEG that are not yet captured by vision-based methods.

Combining BCI with Visual Features

Much recent research has focused on the general problem of combining information from multiple sources. Many feature fusion methods, including Boosting and Bagging, concatenate features extracted from all the modalities to form a single representation, and train a classifier using this joint feature representation. Since the visual category algorithm based on the Pyramid Match Kernel operates at the kernel level, where instead of features the Pyramid Match criterion provides a similarity ($K_A$) between any two given images, it is nontrivial to use such feature-fusion methods in a PMK-dependent framework.

An alternative is to use decision-level fusion, with many possibilities for combining decisions from multiple modalities, including majority vote, sum, product, maximum, and minimum. However, it is difficult to predict which of these fixed rules would perform best. And although there are also methods that adaptively weigh and fuse decisions in an expert-critic framework, such methods undesirably require a large amount of training data.

In an embodiment, a solution is provided in which modalities are fused at the kernel level. Within such embodiment, visual category recognition algorithms are seamlessly combined based on local feature correspondence kernels. For instance, assuming there are similarities (kernels) between vision features and EEG responses, the kernel matrices are additively combined such that the resulting kernel is "ideal" for classification. In a particular embodiment, a formulation for the kernel combination is a convex program, which can naturally handle multiple classes.

In an exemplary method for fusion kernel alignment, given a set of training images and corresponding EEG responses from k different users, the method begins with obtaining kernels that determine the similarity of the images in the visual as well as the EEG signal space. For this method, the aforementioned kernel $K_A$ that describes the computer-processed visual similarity between example images is computed via the Pyramid Match. Further, given EEG responses from a user i it is assumed that the kernel $K_{\epsilon i}$ may be computed which depicts similarity in the ERP space. In FIG. 6, an exemplary human-processed similarity matrix $K_\epsilon$ is provided. For this particular example, a plurality of n images are viewed by a human subject such that similarity matrix $K_\epsilon$ is populated by individual similarity values $K_{\epsilon ij}$, each of which represent similarities between pairs of images i and j. Here, it should be further appreciated that multiple human subjects may be represented by a plurality of similarity matrices $K_{\epsilon 1}, \ldots, K_{\epsilon k}$, where k is the total number of subjects.

Given the kernels $K_A, K_{\epsilon 1}, \ldots, K_{\epsilon k}$, a linear combination of these base kernels is sought such that the resulting kernel K is well-aligned with an ideal kernel A. In an embodiment, ideal kernel A is defined such that the entry $A_{ij}=1$, if and only if the $i^{th}$ and the $j^{th}$ image have the same visual category label, otherwise $A_{ij}=0$. This definition is different from the target kernel used for alignment in earlier approaches. However, those earlier approaches focused on binary classification problems and it is non-trivial to optimize kernels simultaneously when there are more than two classes. Since the proposed target kernel A assigns a value of 0 when the examples belong to different classes, it assumes no similarity between them irrespective of their true labels; thus, allowing the measure to be invariant to the number of classes. Formally, resulting kernel K may thus be computed as:

$$K = \alpha_0 K_\Delta + \sum_{i=1}^{k} \alpha_i K_{\varepsilon i}$$

Here, $\alpha = \{\alpha_0, \ldots, \alpha_k\}$ are parameters that may be optimized. The objective $L(\alpha)$ that is minimized is the squared Frobenius norm of the difference between resulting kernel K and ideal kernel A:

$$\arg\min(\alpha)\|K-A\|_F^2$$

subject to: $\alpha_i \geq 0$ for $i \in \{0, \ldots, k\}$

The non-negativity constraints on a ensure that the resulting kernel K is positive-semidefinite and can be used in an SVM formulation (or other kernel-based methods). The proposed objective is a convex function, which can be readily seen by considering K as a linear combination of vectors constructed by unfolding the basis matrices. With the linear non-negativity constraints, the resulting optimization problem is a convex program and has a unique minimum. Similar criteria has been proposed in the context of Gaussian Processes and Geostatistics. In a manner similar to known alignment measures, it can then be shown that the measure defined by the Frobenius norm is also consistent.

The proposed convex program can be solved using any gradient-descent based procedure. For instance, a gradient descent procedure based on a projected BFGS method that uses a simple line search may be utilized. The gradients of the objective are simple to compute and can be written as:

$$\frac{\delta L(\alpha)}{\delta \alpha i} = 2\text{sum}(K_{\varepsilon i} \cdot (K - A))$$

where sum(•) denotes summation over all the elements of the matrix and the operator ○ denotes the Hadamard product, which is simply the product of corresponding entries in the matrices. Once the parameters a are found, then the resulting linear combination of kernel (K) can be used in any kernel-based learning procedure.

In FIG. 7, an exemplary fused similarity matrix K is provided. For this particular example, it is assumed that a plurality of n images are viewed by a human subject and processed by a computer vision-based system so as to respectively produce similarity matrices $K_\varepsilon$ and $K_A$. Similarity matrix K is then the linear combination of similarity matrices $K_\varepsilon$ and $K_A$ such that individual similarity values $K_{ij}$, each represent fused similarities between pairs of images i and j.

Experimental Results

Various experiments were performed with real-world data to (1) show the advantage of the combined approach, (2) analyze strengths and weaknesses of the two modalities and (3) examine the stability of the combined visual categorization system.

The EEG measurements for these experiments were originally captured using a Biosemi system at 2 kHz from 32 channels. In the Biosemi system, users wear a cap of electrodes placed in the 1020 standard electrode layout shown in FIG. 4. Electrodes measure the electrical activity on the scalp (typically in the microvolt range) and represent a noisy stream of neural activity occurring in the brain.

The images used in the experiments were taken both from the Caltech-256 dataset and from the Internet. For the Animals class, random images from multiple categories of the Caltech256 dataset were chosen. To obtain images for the Inanimate and Face classes, keyword searches on the Internet using the keywords "Face" and "Object" were used. An independent set of people then ranked the collected images according to relevance to the particular category such that the top ranked images were used as stimuli for these classes.

EEG responses were recorded from fourteen users as they viewed the animal, face, and inanimate images while performing a "distracter task," which consisted of counting images that contained butterflies in them. Users were not told of the classification task and were not explicitly trying to perform classification.

The data set consisted of two groups of images drawn from the three categories. The first group (group-1) included sixty images per class shown to each of the subjects only once, whereas the second group (group-2) included twenty images per class which were presented ten times to each subject in a block randomized fashion.

Pyramid Match Kernel computations utilized the libpmk package, which uses SIFT descriptors extracted at salient points in the image, where each descriptor is concatenated with the normalized image position. For computing PMK values, data-dependent partitions were used. The SIFT features were clustered to create a vocabulary tree of depth four and branch factor ten. Using this tree, pyramids were built for each feature set and the match kernel between each pair of images was computed.

EEG measurements were down-sampled to 100 Hz and filtered using a butterworth filter in the range 0.5-30 Hz. Data was restricted to include only the time window 100-500 ms following stimulus presentation. These processing steps are typical of conventional EEG studies which are already known. Also, for this analysis, data from only twelve electrodes of interest 420 were used (CP5, CP6, P3, Pz, P4, P7, P8, PO3, PO4, O1, O2, Oz), since these channels were expected to most closely measure human visual processing activity (electrodes 410 were thus not used). The chosen time window of measurements were concatenated for the channels of interest to form a single vector representing the "EEG feature" for the image. These responses were converted into a similarity measure (i.e., a kernel) by using a gaussian kernel $k(x_i, x_j) = \exp(-\beta\|x_i - x_j\|^2)$, where the scaling factor $\beta = 10^{-5}$ was chosen empirically and kept constant across all experiments and subjects.

The results of the experiments revealed noticeable benefits of combining the two modalities. First, the gains obtained by combining EEG signals with PMK were examined. For this experiment, standard testing protocols for object recognition were followed, where a given number of training images (e.g., 25) are taken from each class at random, and the rest of the data is used for testing. The mean recognition rate was then used as a metric of performance. This process was repeated one hundred times on the group-1 images.

Figure 8:
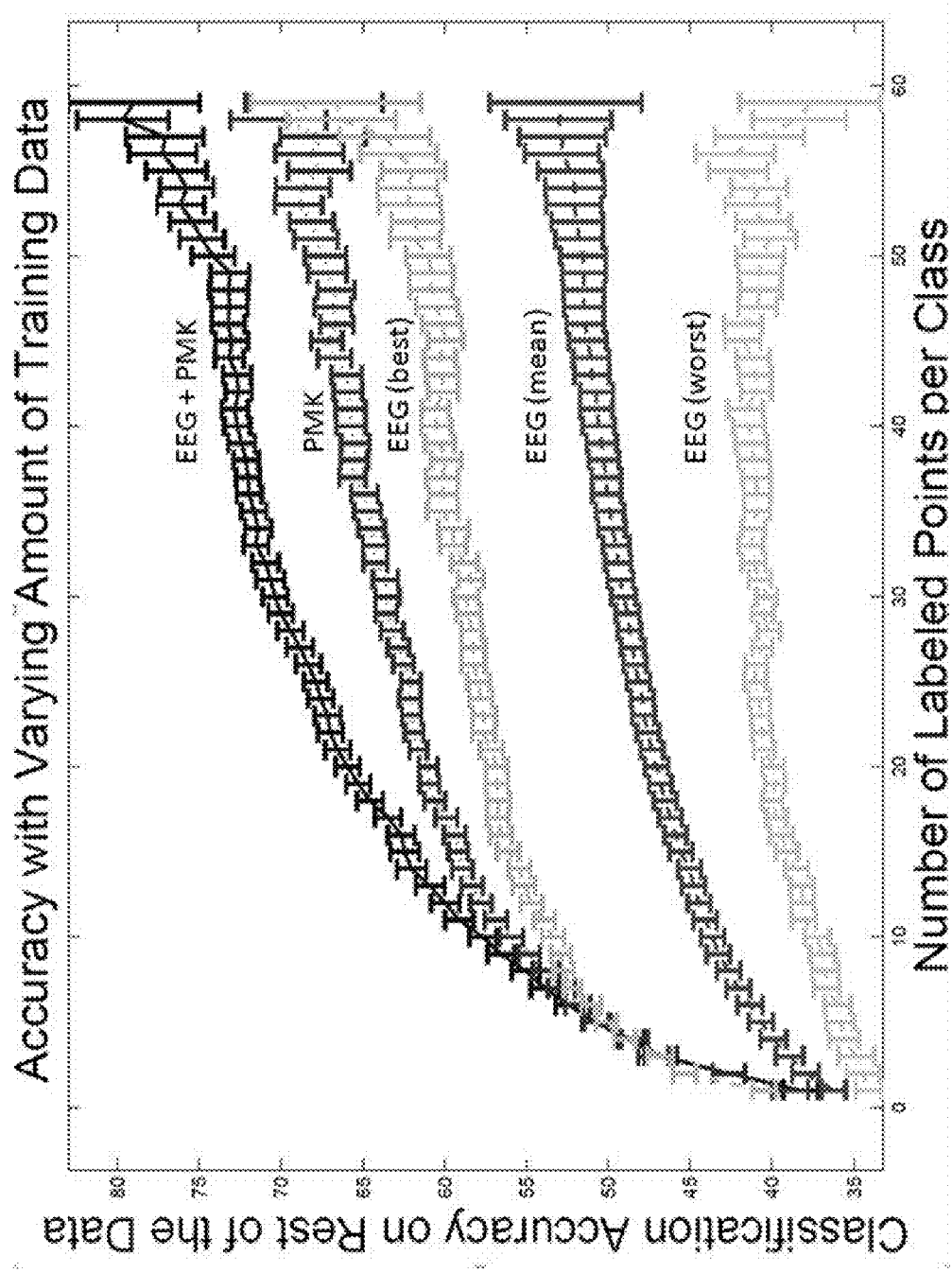
FIG. 8 is a graph illustrating the performance of different modalities on a held-out set of images, where the number of labeled images were varied, in an experiment performed in accordance with an aspect of the disclosed subject matter.

FIG. 8 shows the mean performance for different modalities and the combination, along with the performance of the best and worst of the EEG users. The error bars correspond to standard error scaled by 1.64 and non-overlapping error bars signify 95% confidence in performance difference. As illustrated, significant gains are obtained by combining BCI with vision features. Also, although the vision features consistently outperformed the EEG features, the combination performed better than both individual modalities, suggesting complementary properties between the modalities.

Next, the discriminative power of the different modalities were examined. Specifically, the relative weight $\alpha_0$ of the Pyramid Match Kernel in the kernel combination, was characterized as:

$$\gamma(PMK) = \frac{\alpha_0}{\alpha_0 + \sum_{i=1}^{k} \alpha_i}$$

Similarly, the relative weight for the EEG contribution was characterized as:

$$\gamma(EEG) = 1 - \gamma(PMK)$$

Figure 9:
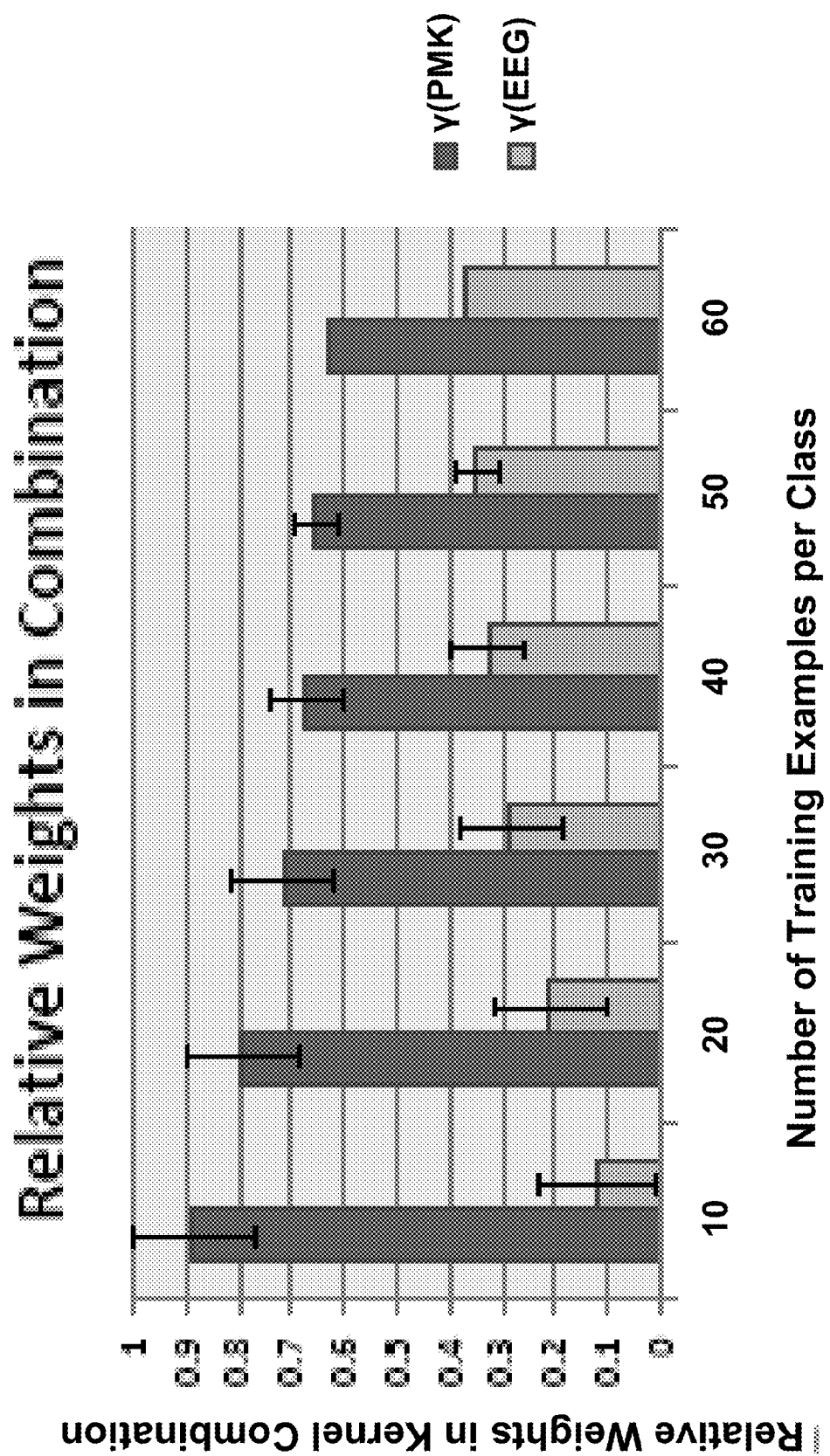
FIG. 9 is a graph illustrating a comparison of relative weights of different modalities, where the number of labeled images per class were varied, in an experiment performed in accordance with an aspect of the disclosed subject matter.

By looking at the statistics of these quantities, estimates for the relative contribution of each modality may be calculated. FIG. 9 shows these relatives weights averaged over 100 different runs (error bars are standard deviation) on group-1 for various amounts of training data. As illustrated, although the vision modality is shown to have higher discriminative power, the relative weight of the EEG modality is highly significant and leads to significant gains in accuracy. Further, the relative contribution of the EEG signal increases with data suggesting that better gains can be expected with more training data.

Next, the distribution of errors made by the different channels and their combinations were examined. To this end, a "leave-one-out" analysis on group-1 images was performed where the system was trained on all the images except a held-out test image. This process was repeated for all the images such that all classification errors made by the system were logged. This analysis was performed for the combined system, the PMK-only system, and a system that uses only EEG data from all the users.

Figure 10:
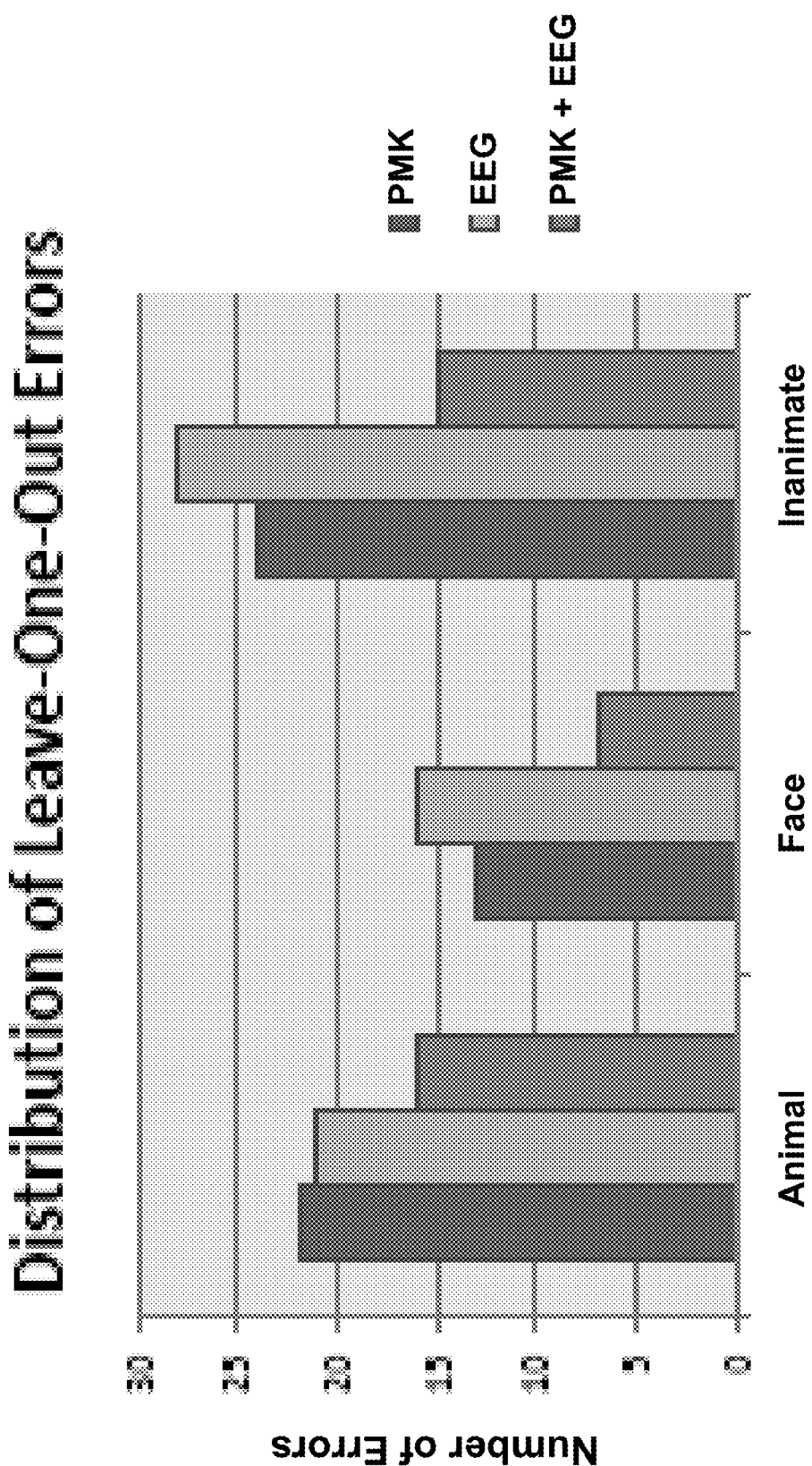
FIG. 10 is a graph illustrating a distribution of errors by individual modalities and their combination resulting from an experiment performed in accordance with an aspect of the disclosed subject matter.

In FIG. 10, a graph illustrating the distribution of errors for this experiment is provided. As illustrated, the combined system consistently reduced the number of errors made across all the classes. Interestingly, when compared to EEG, the PMK modality performed better on the face and the inanimate categories, whereas the EEG modality performed slightly better on the animal category. This might be due to the fact that the face category has enough visual information for a vision-only classifier to work well, whereas the animal images usually have inanimate objects as well in the background that might confuse a vision-only system. The EEG modality on the other hand is more influenced by the semantic association of the image, which allows it to distinguish classes even when the low-level visual features are confusing. Accordingly, although this observation is made on a small data set and needs further study, it is shown that the combination does indeed benefit from individual strengths of both modalities to increase the recognition performance on all the classes.

It should be noted that, since the human brain concurrently handles multiple tasks and may show significant "background activity", significant variations in measured EEG responses, and thus variations in recognition accuracy, were expected. The stability of the combined system in light of these variations were explored. In particular, an analysis was performed on the classification results of group-2 images that were presented to the subjects 10 times each. The classification system was trained on the 180 images from group-1 such that the classification performance was tested with each round of presentation to all the users. In terms of behavior, the classification performance was observed to be similar for all the runs, with the combined system outperforming the individual modalities 9 out of the 10 times.

Figure 11:
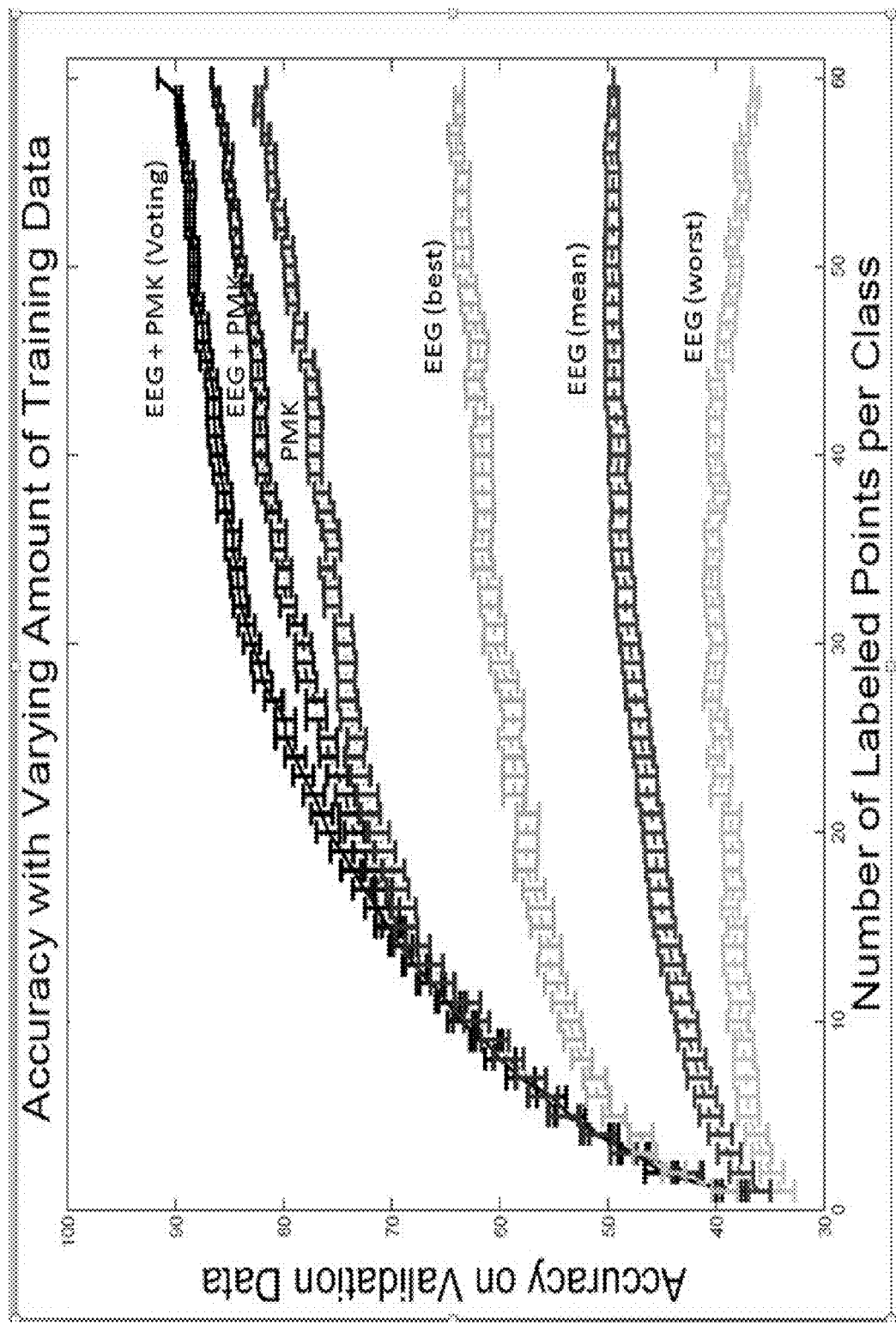
FIG. 11 is a graph illustrating the performance of different modalities on a validation set of images, where the number of labeled images were varied for a single presentation to a subject, in an experiment performed in accordance with an aspect of the disclosed subject matter.

FIG. 11 shows the performance of different modalities for the very first presentation. As illustrated, the performance is similar to the one obtained with group-1 images. Although not provided here, it should be noted that similar curves for the remaining presentations were obtained also obtained. It should be also be noted that the classification accuracy may be further increased by voting (i.e., EEG+PMK+voting) among the presentations and choosing the class label for a test image based on classification agreement across different presentations.

Figure 12:
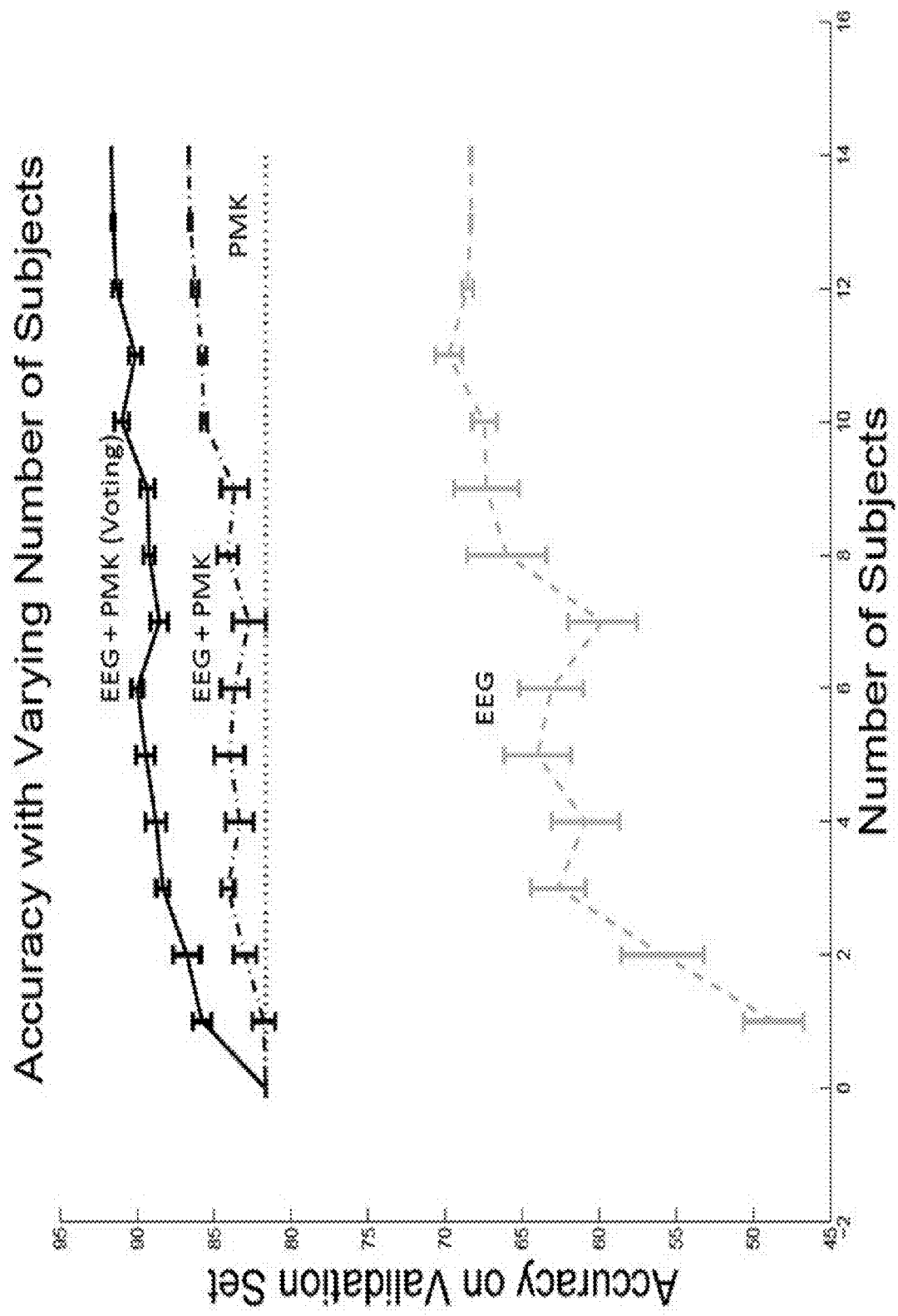
FIG. 12 is a graph illustrating the performance of different modalities on a validation set of images, where the number of subjects were varied, in an experiment performed in accordance with an aspect of the disclosed subject matter.

The number of human-brains required to get a significant boost in accuracy was also examined, as well as how the performance scales as the number of subjects were increased. Again, group-2 was used as the test set for the classifiers trained with the images in group-1. FIG. 12 shows the performance as the number of users is varied, and compares this performance with the baseline performance of the PMK classifier. Each point was generated by averaging over 15 runs, with subjects randomly selected from the group. As before, the error bars signify 95% confidence intervals. As illustrated, a significant boost is achieved with as few as two users and the performance increases almost linearly as EEG data from more subjects is incorporated. Here, it should be noted that the EEG and EEG+PMK curves are shown only for a single presentation to each user. If all 10 presentations are considered and voted on as before, then the performance further improves (EEG+PMK+voting). As illustrated, there is a significant gain for EEG+PMK+voting even with a single user.

Table 1 below summarizes the accuracies obtained on the group-2 images (test set) obtained by classifiers trained on group-1 images. The combination with single presentation outperforms each individual channel with an accuracy of 86.67%. Further improvement is achieved by presenting images to the subjects 10 times and then voting among the outcomes of the 10 combined classifiers.

TABLE 1

Classification accuracies on the validation when trained with 60 labeled examples per class.

| Method | Accuracy |
|---|---|
| PMK | 81.67% |
| EEC | 68.33% |
| PMK + EEC | 86.67% |
| PMK + EEC (VOTING) | 91.67% |

Figure 13:
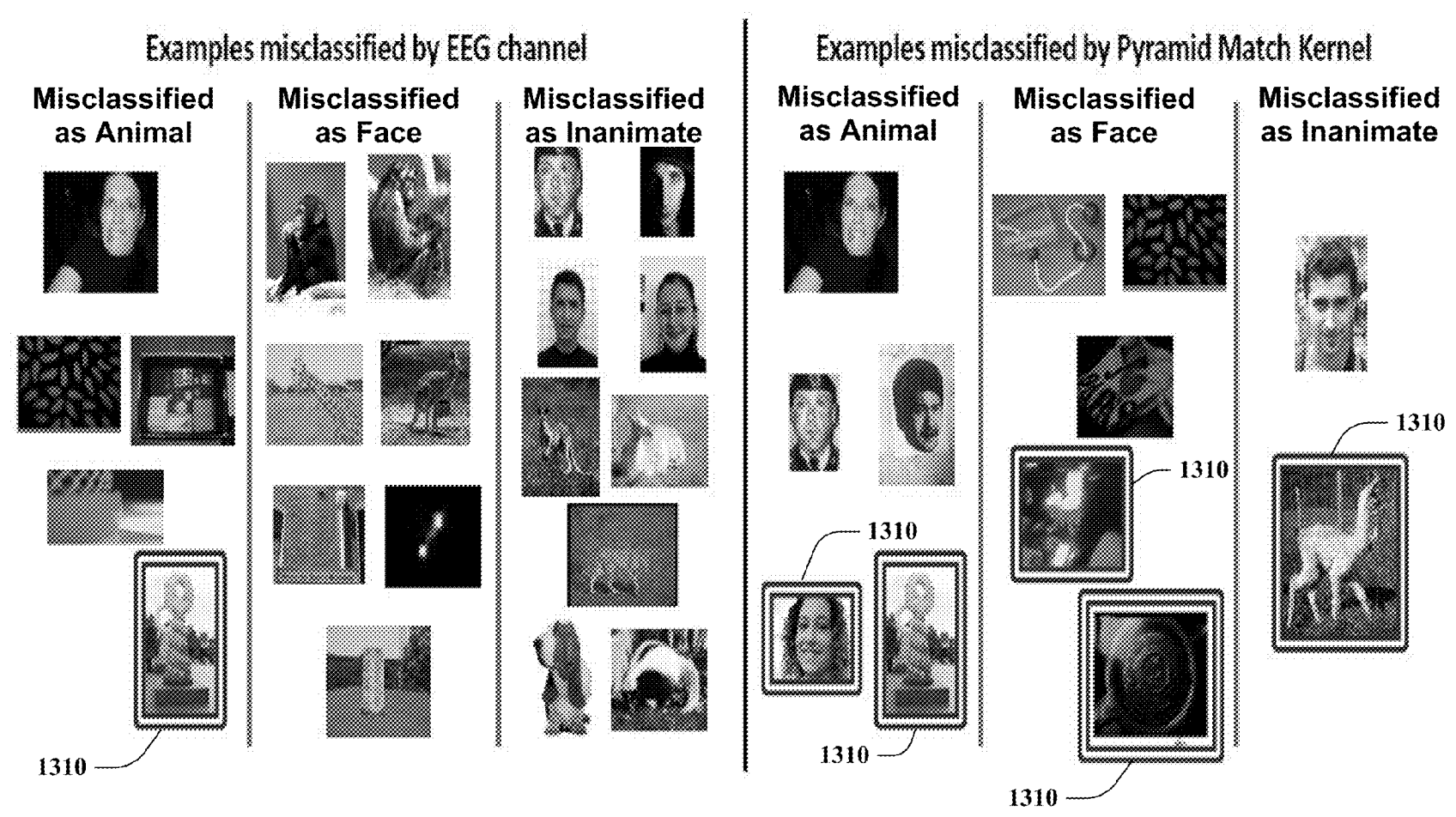

FIG. 13 analyzes different kinds of errors that were made by the different modalities. All errors, except errors 1310, were corrected in the combined system. Furthermore, there were not any additional errors made in the fused system. Interestingly, multiple images illustrating chimps were misclassified as a "face" by the EEG modality. This is not surprising, however, since objects that look similar to faces are known to elicit "face-like" responses in specific areas of the brain.

Multi-View Learning

It should be appreciated that the aforementioned framework for combining human and computer competencies may be utilized to implement a novel multi-view learning method. Indeed, a potential limitation of the aforementioned framework is that it may assume that all data is annotated in advance and that all data channels are always available. The assumption about data completeness, specifying that all computational channels are available, is especially constraining in the discriminative classification setting as it disallows the use of incomplete data. For the task of recognizing objects in images, incomplete data can stem from an image being unlabeled or as yet unprocessed by a human observer.

Figure 14:
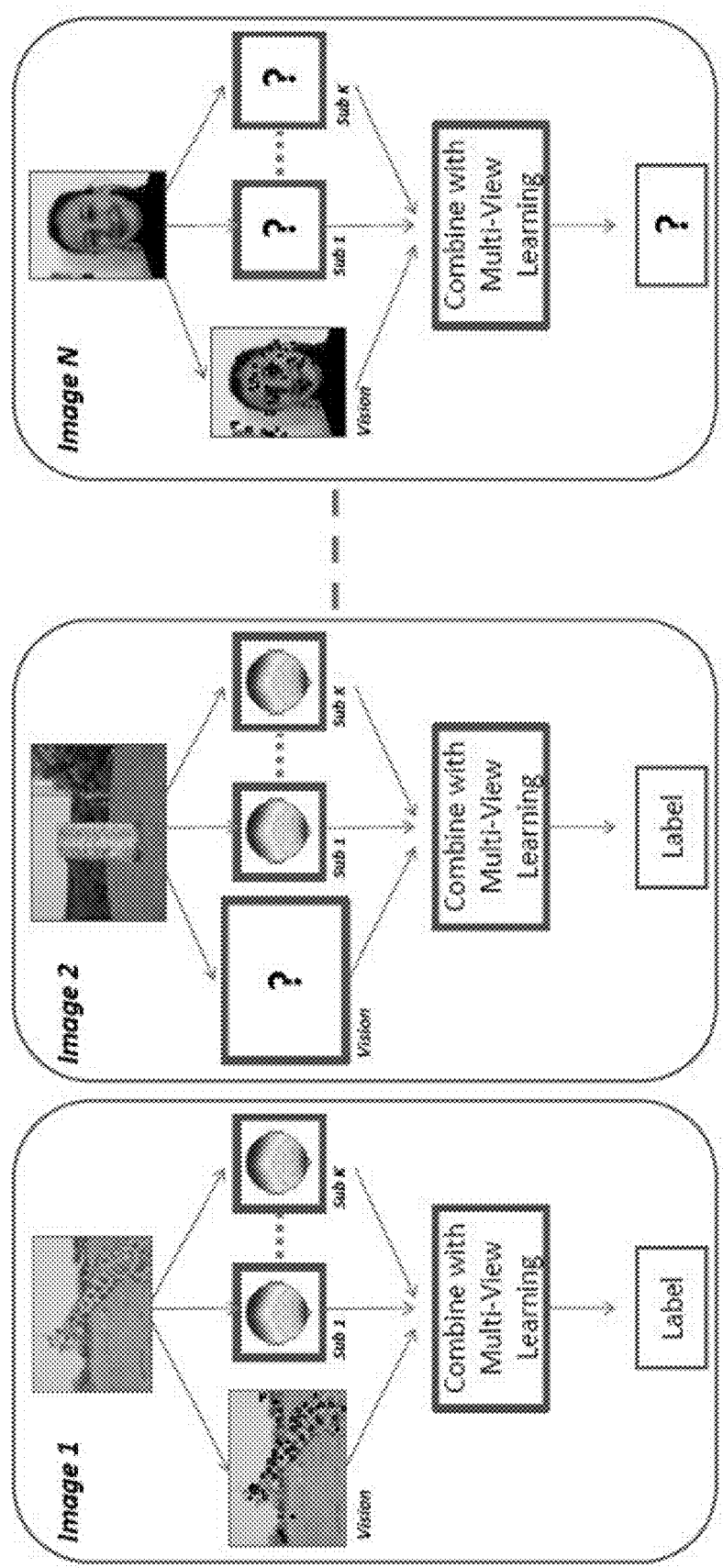
FIG. 14 is an exemplary graphical depiction of a multi-view, human-aided recognition scenario addressed by an aspect of the disclosed subject matter.

In FIG. 14, an exemplary graphical depiction of a multi-view, human-aided recognition scenario addressed by an aspect of the disclosed subject matter is provided. As illustrated, images are again processed by computer vision algorithms and by multiple people, as accessed via EEG signals. Here, however, a method for generating effective predictive models by making use of information from potentially scarce data is provided. A method is also provided for guiding the allocation of labeling and processing resources to achieve a task with minimal overall effort. Moreover, test learning and inference methods are disclosed that support a distributed computing approach, which is potentially robust to the loss of any particular computational processing modality. To do this, a Bayesian co-training model is extended to develop an active-learning method that guides label elicitation and the overall allocation of human and machine computation.

As disclosed herein, an exemplary multi-view learning method is described within the context of (1) providing a theoretically sound and modular multi-view active learning scheme that handles incompleteness and incorporates selective sampling of information to efficiently allocate labeling and processing resources, and (2) providing a concrete instantiation of such a system as applied to human-aided computing.

In an embodiment, the object classification problem is modeled as a multi-view learning task, where each processing modality contributes to a separate view of the data, and is combined in a Bayesian co-training paradigm. The Bayesian co-training paradigm provides a valuable framework for performing joint inferences over all the views without the need for piecewise or iterative training for individual modes. Here, it should be noted that an objective of this particular embodiment is to process each data point selectively by using a carefully selected subset of the views for that data point, thus reducing processing and labeling costs involved in training the classifier. Since the common formulation of expert fusion systems (including co-training) assumes that all of the views for all data points are present, a conventional Bayesian co-training model is adapted to suit the more general situation of missing data.

Figure 15:
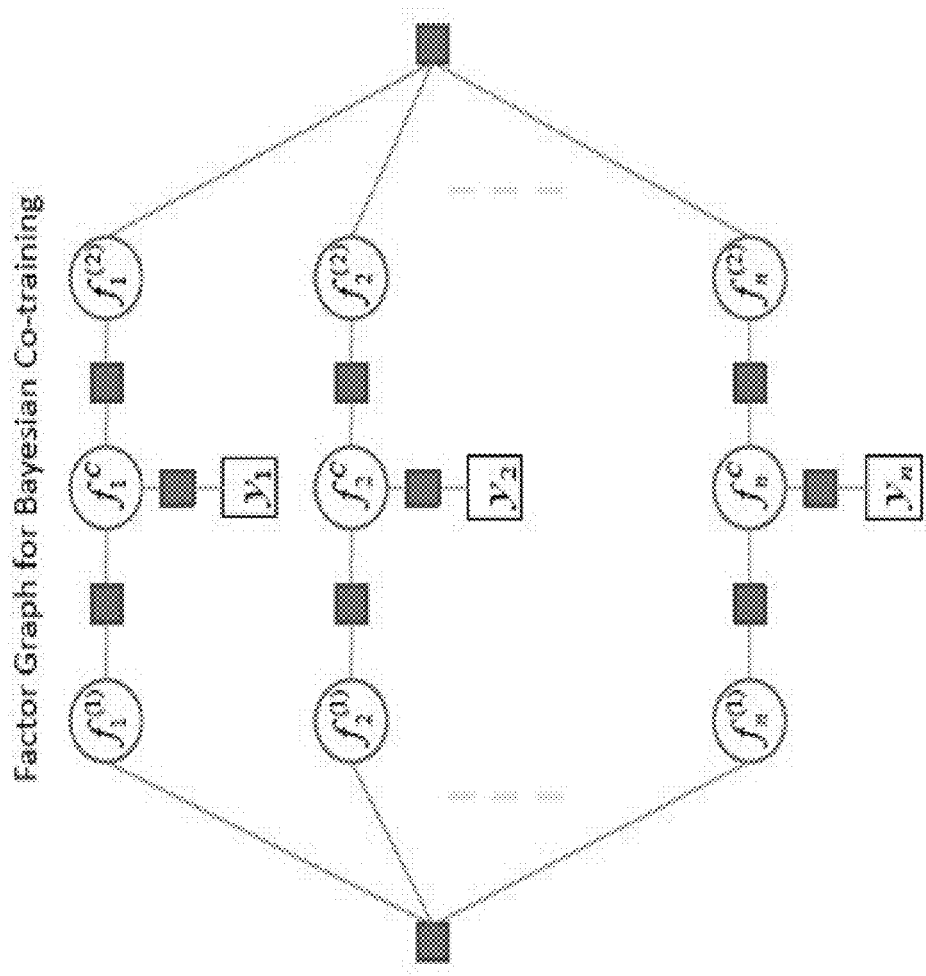
FIG. 15 is an exemplary factor graph corresponding to a Bayesian co-training model with two views in accordance with an aspect of the disclosed subject matter.
Figure 16:
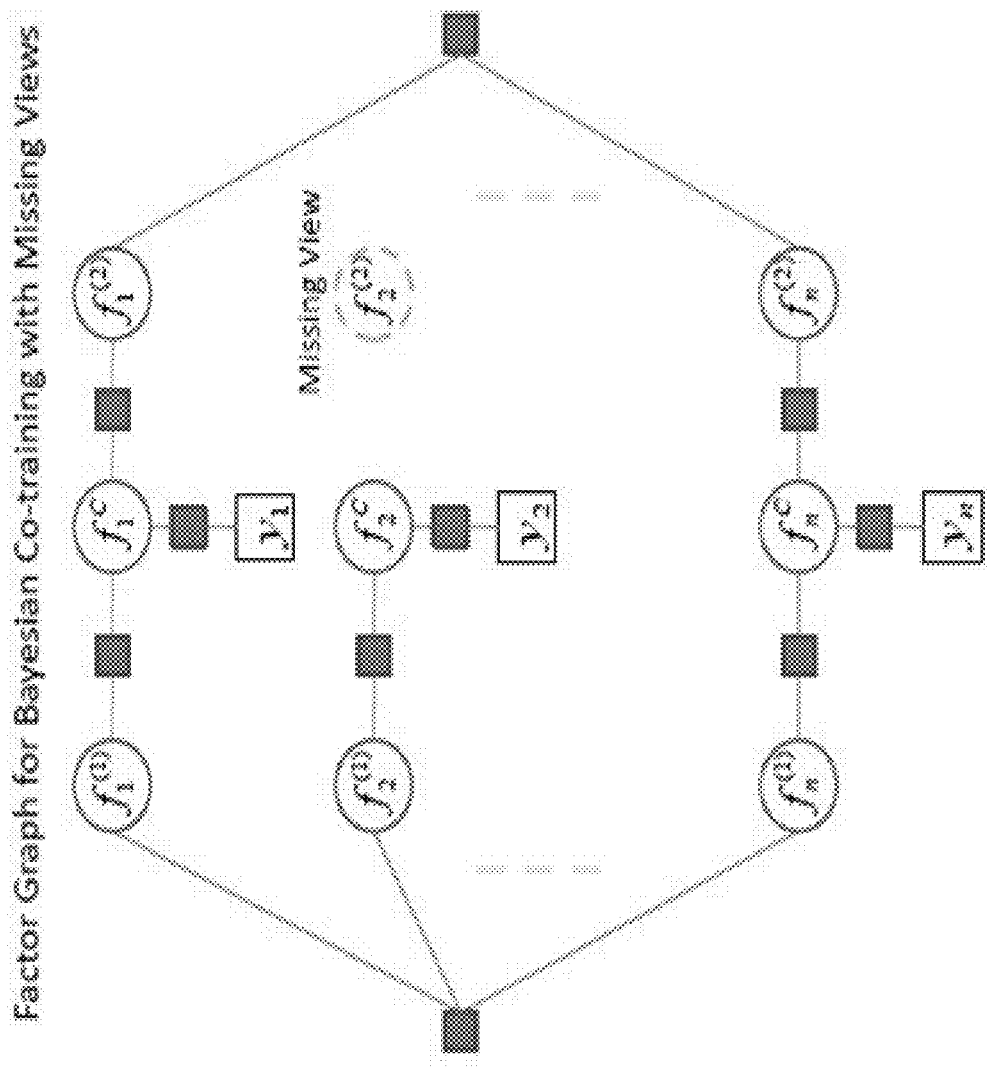
FIG. 16 is an exemplary modification to a factor graph corresponding to a Bayesian co-training model having a missing view in accordance with an aspect of the disclosed subject matter.

In one aspect, the Bayesian formulation of co-training is exploited, where evidence serving as reliability indicators governs the contribution of each modality. By appropriately setting these indicators, the Bayesian co-training model can be extended to jointly handle partially labeled data with incomplete views so as to address the task of active learning. In FIGS. 15 and 16, for instance, exemplary factor graphs corresponding to a Bayesian co-training model with two views is provided. In FIG. 16, however, an exemplary modification to the factor graph in accordance with an aspect of the disclosed subject matter is provided so as to accommodate for a missing view. For instance, in a particular embodiment, the proposed model modification disconnects the nodes corresponding to missing data by appropriately setting the potentials.

Multi-View Learning Background

In traditional multi-view learning or co-training, it is assumed that all of the n training data points have m different views. The Bayesian co-training framework handles multi-view learning by first considering a Gaussian Process prior $\{f^{(1)}, \ldots, f^{(m)}\}$ defined on each of the m different views. Here $f^{(j)}=[f_1^{(j)}, \ldots, f_n^{(j)}]$ is the vector of latent variables corresponding to the $j^{th}$ view for all n data points in the collection. These latent variables are assumed to arise due to a Gaussian Process characterized by a GP prior $f^{(j)} \sim N(0, K^{(j)})$.

Here $K^{(j)}$ is the kernel matrix computed using features only from view j. In FIG. 17, an exemplary single-view similarity matrix $K^{(j)}$ in accordance with an aspect of the disclosed subject matter is provided. For this particular example, n images are processed by a single modality. In an embodiment, this modality could either be a human subject or computerized vision-based processor such that similarity matrix $K^{(j)}$ is populated by individual similarity values $K^{(j)}_{xy}$, each of which represent similarities between pairs of images x and y for the $j^{th}$ view.

Despite multiple views, each data point has only a single label and thus the final class label should depend on all of these latent function values for that data point. This is ensured via consensus latent variables $f^C$, which aggregate information coming through all the different views and influence the final output. Specifically, the final outputs $y=[y_1, \ldots, y_n]$ for all n data points only depend on the consensus latent variables. Formally, the joint distribution of the latent variables and the output over all the data points can be written in the following factorized form:

$$p(y, f^C, f^{(1)}, \ldots, f^{(m)}) = \frac{1}{Z} \prod_{i=1}^{n} \psi(y_i, f_i^C) \prod_{j=1}^{m} \psi(f^{(j)}) \psi(f^{(j)}, f^C)$$

Here, Z is the normalization term. The potential $\psi(f^{(j)}) \sim N(0, K^{(j)})$ arises due to the GP prior and specifies view constraints for the latent variables. Intuitively, this enforces the constraint that the latent variables in a particular view should co-vary according to the similarities specified by the kernel matrix $K^{(j)}$. On the other hand, the potential $\psi(f^{(j)}, f^C)$ defines the compatibility between the $j^{th}$ view and the consensus function and can be written as:

$$\psi(f^{(j)}, f^C) = \exp\left(-\frac{\|f^{(j)} - f^C\|^2}{2\sigma_j^2}\right)$$

Here, the parameters $\alpha_j$ act as reliability indicators and control the strength of interaction between the $j^{th}$ view and the consensus latent variable. A small value of $\alpha_j$ imposes a strong influence of the view on the final output, whereas a very large value allows the model to discount observations from that view. Finally, the potential $\psi(y_i, f_i^C)$ defines the dependence of the consensus variable and the final output. Similar to GP models this can either be a Gaussian noise model or a classification likelihood defined via a link function (e.g., probit or logistic function). Experiments performed in accordance with aspects of the disclosed subject matter utilized a Gaussian noise model parameterized by $\alpha_C$ for simplicity. Nevertheless, it should be appreciated that use of a probit or logistic model is also feasible.

An advantage of utilizing a Bayesian co-training model is the ability to marginalize over the latent variables $\{f^{(1)}, \ldots, f^{(m)}\}$ corresponding to views and obtain a Gaussian prior on the consensus latent variables directly. That is, $$p(f^C) \sim N(0, K^C) \text{ where: } K^C = [\Sigma_{j=1}^{m}(K^{(j)} + \alpha_j^2)^{-1}]^{-1}$$

This implies that given multiple views of all the data points a co-training kernel $K^C$ can be computed as above and can be directly used for Gaussian Process classification or regression. Unlike other co-training algorithms that require alternating optimizations, Bayesian co-training allows for jointly optimizing all the views simultaneously. Furthermore, this consensus kernel naturally handles semi-supervised settings as the kernel $K^C$ is non-stationary and is dependent on both labeled and unlabeled data. In FIG. 18, an exemplary multi-view similarity matrix $K^C$ in accordance with an aspect of the disclosed subject matter is provided. For this particular example, n images are processed by m modalities, which may include any combination of human subjects and/or computerized vision-based processors. Within such embodiment, similarity matrix $K^C$ is populated by individual similarity values $K^C_{x,y}$, each of which represent consensus similarities between pairs of images x and y for m views.

Multi-View Learning with Incomplete Data

It should be noted that the formulations for co-training described above assume that all of the views are observed for all of the data points. By design, such a model is thus generally inapplicable to scenarios where the processing of each image via all computational modes is not expected. To better understand this limitation, assume that only a subset of views available for point $x_i$ is observed. If $Q_i$ denotes the set of missing views for the $i^{th}$ data point, then the entire row/column $K_{(i)}^{(j)}$ for all $j \in Q_i$ cannot be computed. In the discriminative setting, because the underlying distribution of the data is never modeled, it is not possible to estimate those missing values. This in turn implies that the kernel matrices for all of the views $j \in Q_i$ are incomplete and that the consensus matrix $K^C$ cannot be computed unless the $i^{th}$ data point is completely ignored.

Such a choice is suboptimal since the remaining observed views for the data points are not utilized in building the classifier. For instance, in FIG. 19 illustrations of a complete single-view similarity matrix and two incomplete single-view similarity matrices are provided. For this particular scenario, similarity matrix $K^{(a)}$ provides a complete set of "a" views for each of images 1 through n, whereas similarity matrix $K^{(b)}$ is missing a "b" view of image 2 and similarity matrix $K^{(c)}$ is missing a "c" view of image 3. As such, a consensus matrix $K^C$ cannot be computed unless each of images 2 and 3 are completely ignored. This is inefficient since each of matrices $K^{(a)}$ and $K^{(c)}$ include views of image 2, and each of matrices $K^{(a)}$ and $K^{(b)}$ include views of image 3.

In an embodiment, this problem is resolved via the parameter $\alpha_j$ which determines compatibility of the $j^{th}$ view with the consensus latent variable and acts as a reliability indicator. A key insight to note here is that a high value of $\alpha_j$ minimizes the influence of the $j^{th}$ view on the final result, whereas a small value emphasizes information from that particular view. Therefore, in one aspect of the disclosed subject matter, a strategy for handling an unobserved view includes replacing the parameter $\alpha_j$ with the parameter $\alpha_x$, which has a very large value (e.g., tends to $\infty$). Formally, such strategy may include the following characterization $$\psi(f_i^{(j)}, f^C) = \exp\left(-\frac{(f_i^{(j)} - f^C)^2}{2\alpha_{ij}^2}\right)$$

$$\text{where } \alpha_{ij} = \begin{cases} \alpha_j & \text{if } jth \text{ view available for } ith \text{ data} \\ \alpha_x & \text{Otherwise} \end{cases}$$

In one embodiment, the large parameter $\alpha_x$ is only used for those examples with missing views, leaving the parameters unchanged for the rest of the data. An appealing property of this formulation is that as $\alpha_x$ becomes large, the missing entries $K_{(i)}^{(j)}$ become irrelevant.

Referring next to FIG. 20 an illustration of a complete single-view similarity matrix and two proxy-filled single-view similarity matrices in accordance with an aspect of the disclosed subject matter is provided. For this particular scenario, similar to FIG. 19, matrix $K^{(a)}$ provides a complete set of "a" views for each of images 1 through n, whereas similarity matrix $K^{(b)}$ is missing a "b" view of image 2 and similarity matrix $K^{(c)}$ is missing a "c" view of image 3. Here, however, a consensus matrix $K^C$ can indeed be computed since proxy values are provided for each of the missing views by respectively setting the corresponding $\alpha_j$ values to a high value. Moreover, consensus matrix $K^C$ is calculated such that the respective influences of the missing views on the final result are minimized. As a result, each of images 1, 2, and 3 can now be used.

In fact, it may be shown that, in the limit $\alpha_x \to \infty$, the co-training kernel $K^C$ reduces to the following form:

$$\lim_{\alpha_x \to \infty} K^C = \left[\sum_{j=1}^{m} R^{(j)}\right]^{-1}$$

Here, $R^{(j)}$ is the pseudoinverse of $(K^{(j)} + \alpha_j^2)$ where all the rows and columns of $K^{(j)}$ corresponding to the missing entries are set to zero. Hence, under this limit, it is feasible to compute $K^C$ even without knowing the missing entries. Further, if there is at least one view available for all of the points, the resulting matrix is positive semidefinite. This implies that the resulting matrix $K^C$ is a valid kernel, and can be used with any kernel-based learning mechanism.

Intuitively, the original Bayesian co-training model works by appropriately weighting each view by considering the individual beliefs about the final result. By setting noise parameters as described above, the co-training model ignores any contribution when a view is missing while letting other available views influence the decision. Thus, the model appropriately fuses information whenever it is present and helps to classify unlabeled data by leveraging the co-training paradigm. This model is appropriate for human-aided computing, where people are an integral part of the problem solving system. The approach is fundamentally flexible and modular as classification can progress with the loss of individual computing modalities. This Bayesian formulation also provides a way for exploring different models for active learning using various information-theoretic policies.

Active Information Seeking

Existing methods for active learning includes approaches designed for multi-view learning. However, besides assuming that all of the features and views are fully observed, most of these approaches are focused solely on label elicitation. As described earlier, a human can participate in the classification system by either providing annotations for unlabeled data or by providing computation via the brain activities associated with transforming optical information into EEG signals. An annotation directly contributes to the task of training by extending the library of labeled examples, whereas the implicit brain-processing can provide additional features at a relatively quicker pace. While the deliberate annotation of a sample challenge image might take a human several seconds to complete, a brain response can potentially be recorded in a fraction of a second. Accordingly, in one aspect of the disclosed subject matter, the active information collection task is to determine the next interaction a human should perform in order to maximally improve the classification performance.

To this end, existing ideas are borrowed from work on active learning to selectively seek the most useful interaction from a human. Within the Bayesian classification paradigm, heuristics such as entropy and information gain have been popular. As such, consider the following example where X denotes a set of random variables that are currently unobserved, and T is the set of random variable that a researcher is most interested in learning about. For example, T can be a set of labels for the test points. Then, the active learning criteria can be written as following:

Entropy: $X^* = \arg\max H(X)$

Information Gain: $X^* = \arg\max MI(T,X)$

Here H(X) and MI(T, X) represent functions that compute entropy and mutual information respectively. These formulations are general and can be used to perform non-myopic selective sampling where a subset of random variables are chosen together instead of just one. In the experiments that follow, however, myopic selective sampling is used.

Using the co-training kernel, the techniques described above can be used to selectively sample data points for labeling information. However, determining which view to probe next is a more challenging problem since the Gaussian Process classification framework does not model the underlying data density, and it is infeasible to compute the active learning criteria. One possibility is to maintain a generative model to capture the underlying distribution of observations for each view, at the cost of the advantages that are provided by the discriminative classification paradigm.

In one embodiment, however, it is instead noticed that for every $i^{th}$ data point with the $j^{th}$ view missing, the underlying latent variables $f_i^{(j)}$ is modeled. As such, these latent variables can be used as surrogates to compute the active learning criterion so as to determine the next data point and its corresponding view to be observed. Formally, if $\mu$ denotes the set of missing labels and missing views corresponding to every $j^{th}$ human, $X_j$ can be defined as:

$$X_j = \left\{ \bigcup_{y_i \in \mu} y_i \right\} \cup \left\{ \bigcup_{f_i^{(j)} \in \mu} f_i^{(j)} \right\}$$

Figure 21:
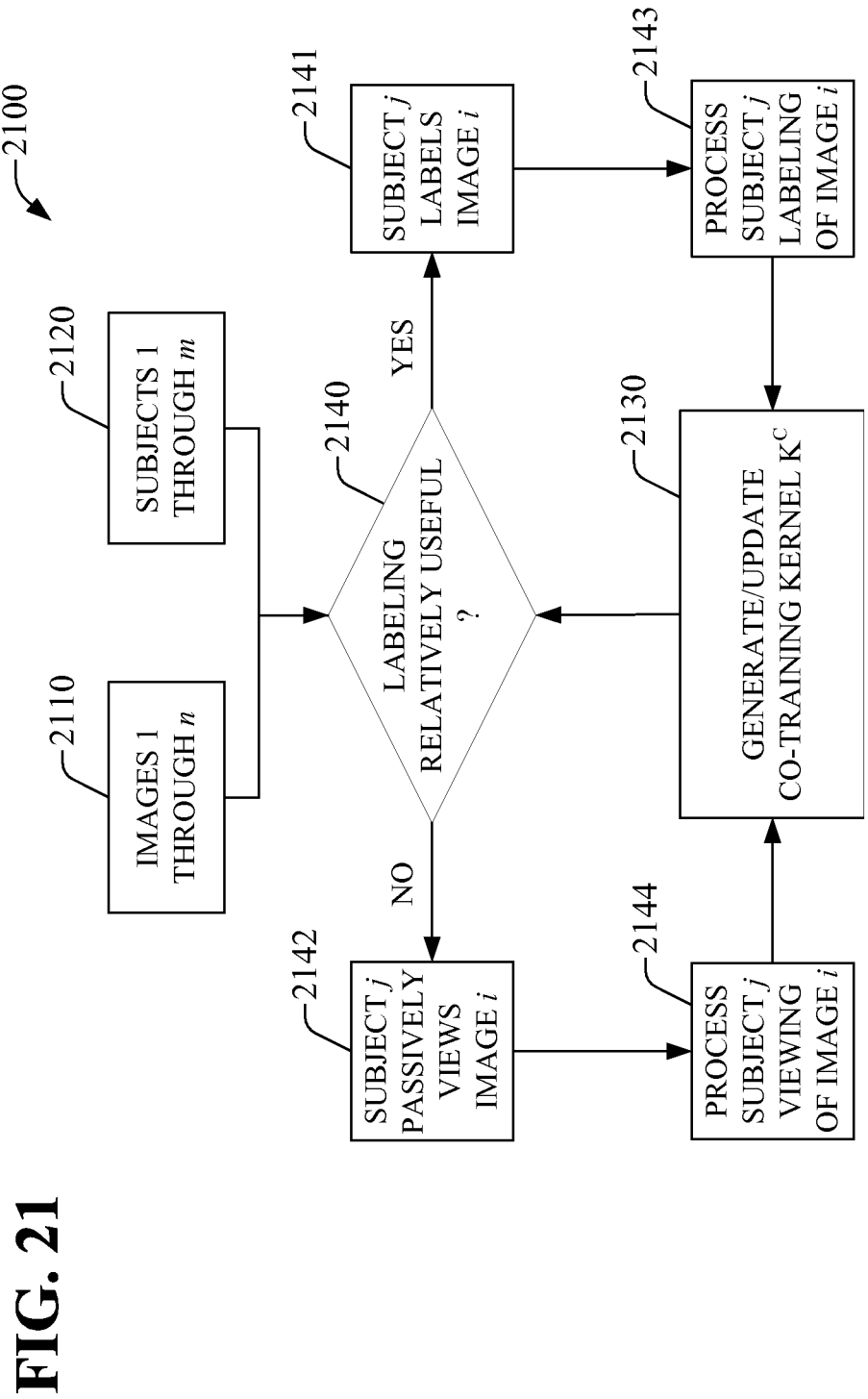
FIG. 21 is a flow chart illustrating an exemplary active information seeking methodology in accordance with an aspect of the disclosed subject matter.

The disclosed system can thus exploit the active learning paradigm to appropriately allocate human resources to train the classification system with minimal cost. In FIG. 21, a flow chart illustrating an exemplary active information seeking methodology in accordance with an aspect of the disclosed subject matter, is provided. As illustrated, methodology 2100 includes a determination at step 2140 of whether requesting a human subject to label a particular image is more useful/efficient than simply allowing the subject to passively view the image. Within such embodiment, this determination is made as a function of information as to the particular image provided at step 2110, information as to the particular subject viewing the image provided at step 2120, and information as to the current status of $K^C$ provided at step 2130.

If at step 2140, it is determined that a particular image i should be annotated by a particular subject j, methodology 2100 proceeds to step 2141 where the annotation is performed. The data corresponding to the annotation performed at step 2141 is then processed at step 2143 and subsequently used to update $K^C$ at step 2130. If, however, it is determined that a particular image i should not be annotated, methodology 2100 proceeds to step 2142 where image i is passively viewed by subject j. The data corresponding to the visualization performed at step 2142 is then processed at step 2144 and subsequently used to update $K^C$ at step 2130. Once the status of $K^C$ has been updated with the processing of image i, either via passively viewing the image or annotating the image, a subsequent image is input and the process is repeated.

It should be appreciated that the aforementioned paradigm can be also applied to nonhuman computational resources, albeit with the exception that those resources cannot provide annotations. For example, rather than assuming availability of the vision features for all images, the visual feature extraction can be applied in an ordered sequence to minimize computational effort. Thus, the presented system can allocate both human and machine resources appropriately for the purpose of efficient learning. It should also be noted that each modality performs resource allocation independently and that a scheduling mechanism can also be contemplated.

Experimental Results

Next, a summary of several results obtained from performing experiments in accordance with the disclosed subject matter is provided. In particular, results are provided in accordance with experiments performed to explore (1) the classification performance in the presence of incomplete views, (2) the benefits of active learning, and (3) how vision algorithms can be improved by harnessing human computation. The EEG and image data for these experiments were taken from the previous experiments performed for determining the performance of the fused human/computer processing method.

Figure 22:
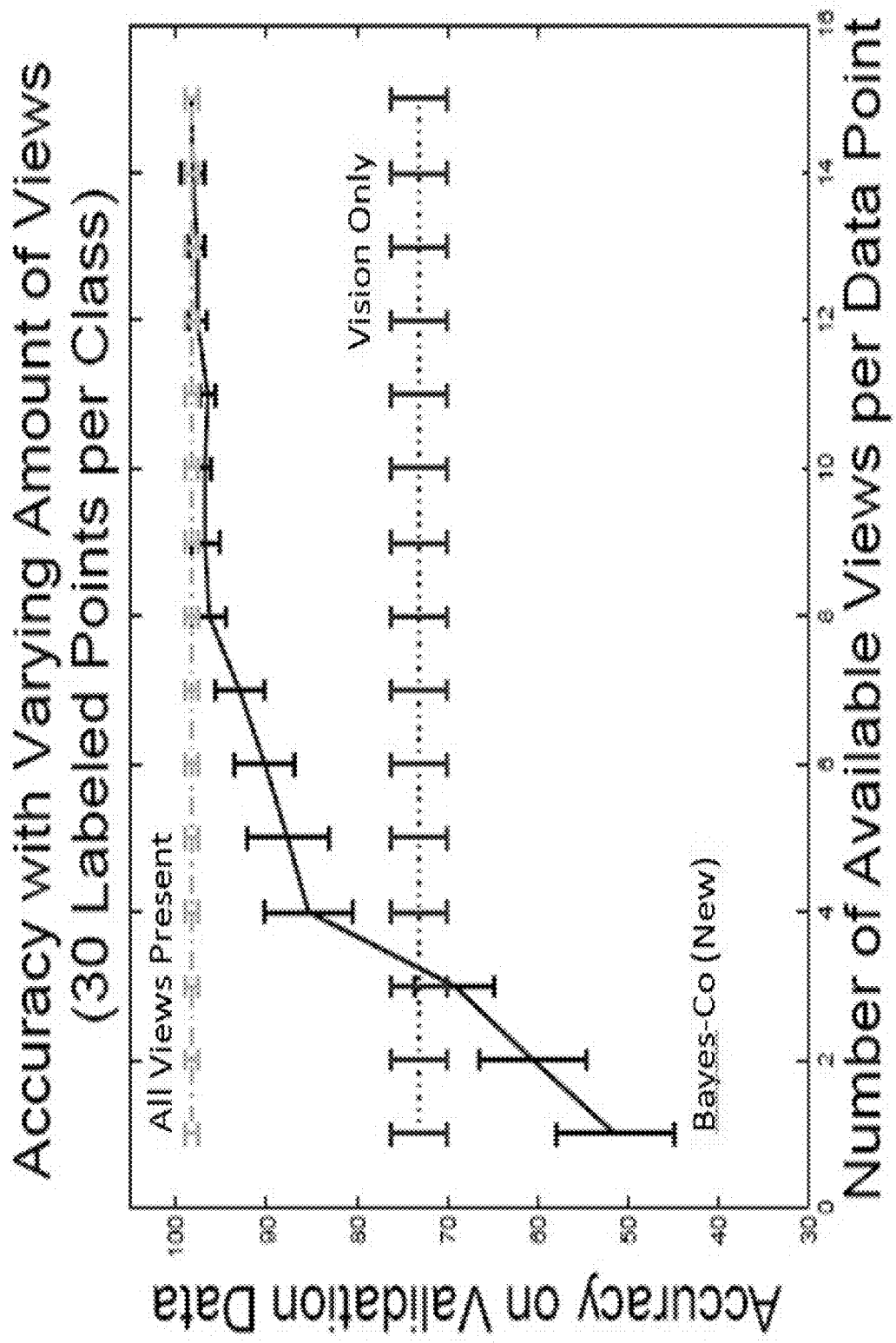
FIG. 22 is a graph illustrating classification accuracy of an exemplary system in light of missing views from an experiment performed in accordance with an aspect of the disclosed subject matter.

Experimentation began by demonstrating that the proposed system can successfully perform even when there were views missing at train or test time. FIG. 22 shows classification accuracy on the test set as the number of available views are varied. To generate this plot, subsets of views for every data point were randomly selected from the training set. The results were averaged over 10 different runs and non-overlapping error bars (standard error scaled by 1.64) signify 95% confidence in performance difference. As illustrated, even with an average of only 8 views present per data point, the proposed framework still achieved similar accuracies to the case where all of the views were present. These results thus demonstrate how the disclosed model exploits redundancies in views and propagates information in light of incompleteness.

Figure 23:
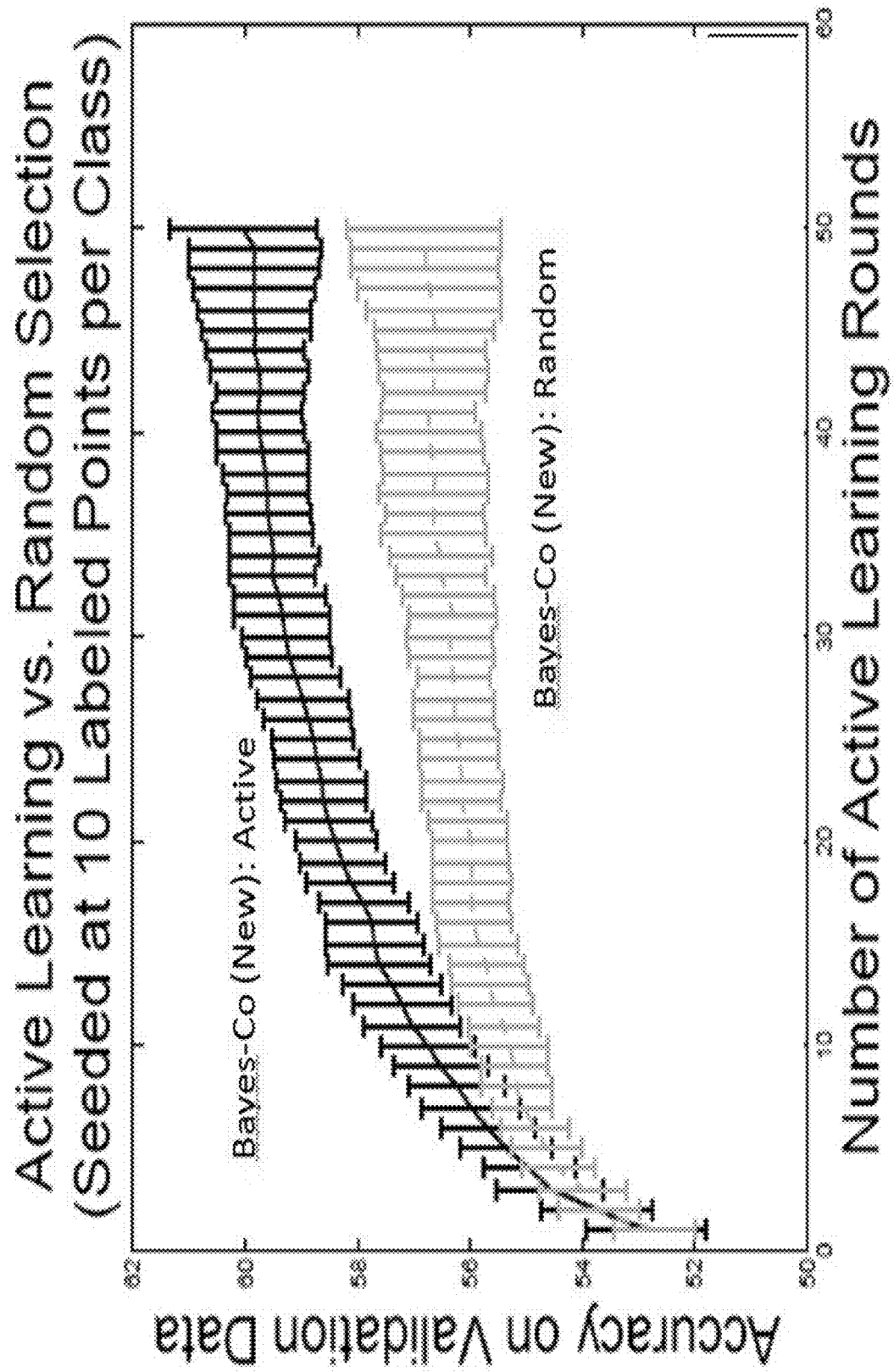
FIG. 23 is a graph quantitatively illustrating benefits of active information selection in accordance with an aspect of the disclosed subject matter.

To explore the value of active learning, the classification performance on the test set was analyzed as each processing modality selected the next action to take. The active learning scheme was compared against a strategy of letting each processing modality select an action randomly. Furthermore, assuming that the time required to annotate an image (~500 ms) is ten times more than the time required for brain computation (~50 ms), the chance that a random strategy selects annotation is ten times lower than the chance that a human would provide brain computation. Similarly, one label annotation was interleaved for every 10 rounds of active learning. The algorithm was randomly seeded by selecting 10 images having labels, assuming that 50% of the views were observed for each instance. FIG. 23 shows the classification performance averaged over 100 different runs as different processing modalities choose to provide either a label or processing power in order to compute an unobserved view in every round. It should be noted that a significant boost in performance was observed in comparison to the random selection of views. These experiments thus demonstrate the effectiveness of the selective information seeking scheme in order to boost performance at a minimum cost.

Figure 24:
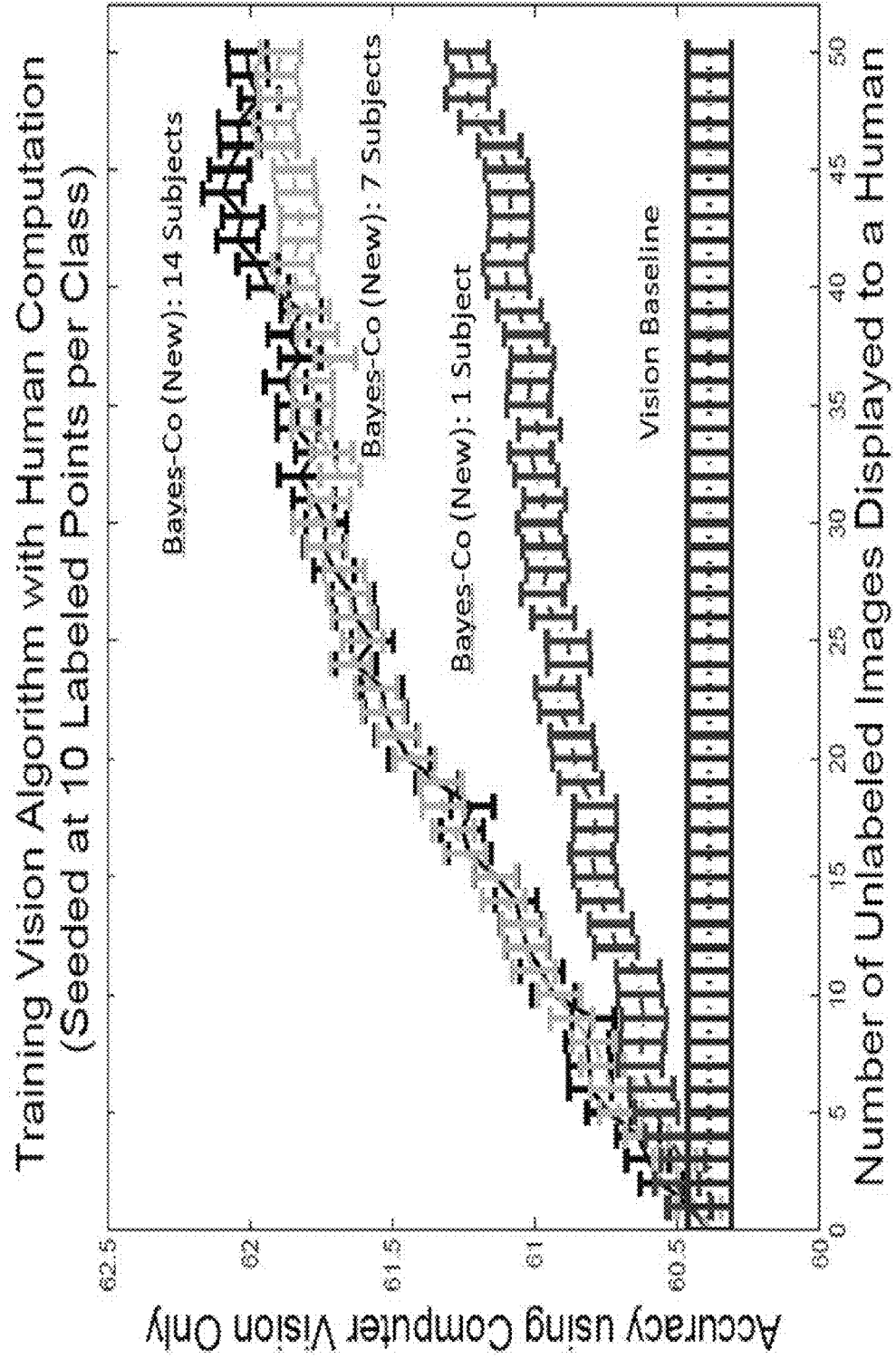
FIG. 24 is a graph illustrating the benefits of training a pure vision system with human computation in accordance with an aspect of the disclosed subject matter.

With respect to experimenting how vision algorithms can be improved via human computation, a scenario where only a subset of the images have been labeled is considered such that the value of presenting the rest of the unlabeled images to humans is explored so as to boost recognition, based solely on the use of the computer-vision algorithm. Moreover, an objective of this experiment was to train a computer-vision system with implicit processing (i.e., without requiring manual annotation of images). FIG. 24 shows the accuracy of classification for the test set as the number of images from the unlabeled pool that are presented to users are varied (starting with a randomly selected set of ten images that were labeled and processed). These results were reported by averaging over 1000 runs to show performance of recognition with only the computer vision modality (i.e., for test set only vision features were used). Different curves in the figure correspond to different numbers of randomly selected people contributing brain processing. As illustrated, the accuracy of the classification using only computer vision increased even when unlabeled images were presented to subjects. Furthermore, significant gains are observed with just a single human observer and the classification accuracy also increases as additional participants are included. FIG. 24 also illustrates that this gain in accuracy saturates with 40 humans, which suggests that there is correlation among EEG signals collected from different users. These experiments thus demonstrate that brain computation can boost the accuracy of a computer-vision classification system significantly.

Exemplary Networked and Distributed Environments

One of ordinary skill in the art can appreciate that the various embodiments described herein can be implemented in connection with any computer or other client or server device, which can be deployed as part of a computer network or in a distributed computing environment, and can be connected to any kind of data store. In this regard, the various embodiments described herein can be implemented in any computer system or environment having any number of memory or storage units, and any number of applications and processes occurring across any number of storage units. This includes, but is not limited to, an environment with server computers and client computers deployed in a network environment or a distributed computing environment, having remote or local storage.

Distributed computing provides sharing of computer resources and services by communicative exchange among computing devices and systems. These resources and services include the exchange of information, cache storage and disk storage for objects, such as files. These resources and services also include the sharing of processing power across multiple processing units for load balancing, expansion of resources, specialization of processing, and the like. Distributed computing takes advantage of network connectivity, allowing clients to leverage their collective power to benefit the entire enterprise. In this regard, a variety of devices may have applications, objects or resources that may cooperate to perform one or more aspects of any of the various embodiments of the subject disclosure.

Figure 25:
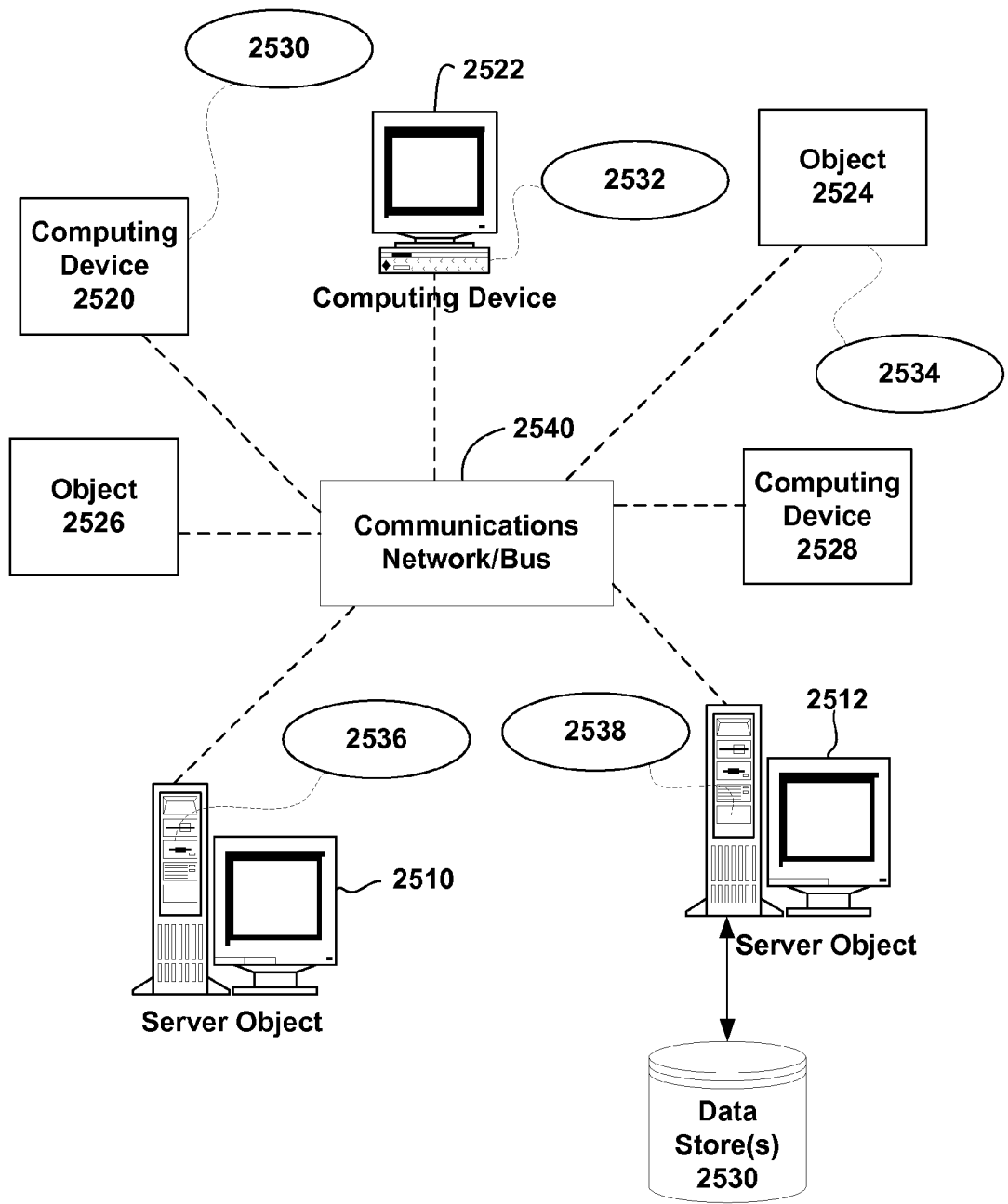
FIG. 25 is a block diagram representing exemplary non-limiting networked environments in which various embodiments described herein can be implemented.

FIG. 25 provides a schematic diagram of an exemplary networked or distributed computing environment. The distributed computing environment comprises computing objects 2510, 2512, etc. and computing objects or devices 2520, 2522, 2524, 2526, 2528, etc., which may include programs, methods, data stores, programmable logic, etc., as represented by applications 2530, 2532, 2534, 2536, 2538. It can be appreciated that objects 2510, 2512, etc. and computing objects or devices 2520, 2522, 2524, 2526, 2528, etc. may comprise different devices, such as PDAs, audio/video devices, mobile phones, MP3 players, personal computers, laptops, etc.

Each object 2510, 2512, etc. and computing objects or devices 2520, 2522, 2524, 2526, 2528, etc. can communicate with one or more other objects 2510, 2512, etc. and computing objects or devices 2520, 2522, 2524, 2526, 2528, etc. by way of the communications network 2540, either directly or indirectly. Even though illustrated as a single element in FIG. 25, network 2540 may comprise other computing objects and computing devices that provide services to the system of FIG. 25, and/or may represent multiple interconnected networks, which are not shown. Each object 2510, 2512, etc. or 2520, 2522, 2524, 2526, 2528, etc. can also contain an application, such as applications 2530, 2532, 2534, 2536, 2538, that might make use of an API, or other object, software, firmware and/or hardware, suitable for communication with, processing for, or implementation of the column based encoding and query processing provided in accordance with various embodiments of the subject disclosure.

There are a variety of systems, components, and network configurations that support distributed computing environments. For example, computing systems can be connected together by wired or wireless systems, by local networks or widely distributed networks. Currently, many networks are coupled to the Internet, which provides an infrastructure for widely distributed computing and encompasses many different networks, though any network infrastructure can be used for exemplary communications made incident to the column based encoding and query processing as described in various embodiments.

Thus, a host of network topologies and network infrastructures, such as client/server, peer-to-peer, or hybrid architectures, can be utilized. The "client" is a member of a class or group that uses the services of another class or group to which it is not related. A client can be a process, i.e., roughly a set of instructions or tasks, that requests a service provided by another program or process. The client process utilizes the requested service without having to "know" any working details about the other program or the service itself.

In a client/server architecture, particularly a networked system, a client is usually a computer that accesses shared network resources provided by another computer, e.g., a server. In the illustration of FIG. 25, as a non-limiting example, computers 2520, 2522, 2524, 2526, 2528, etc. can be thought of as clients and computers 2510, 2512, etc. can be thought of as servers where servers 2510, 2512, etc. provide data services, such as receiving data from client computers 2520, 2522, 2524, 2526, 2528, etc., storing of data, processing of data, transmitting data to client computers 2520, 2522, 2524, 2526, 2528, etc., although any computer can be considered a client, a server, or both, depending on the circumstances. Any of these computing devices may be processing data, encoding data, querying data or requesting services or tasks that may implicate the column based encoding and query processing as described herein for one or more embodiments.

A server is typically a remote computer system accessible over a remote or local network, such as the Internet or wireless network infrastructures. The client process may be active in a first computer system, and the server process may be active in a second computer system, communicating with one another over a communications medium, thus providing distributed functionality and allowing multiple clients to take advantage of the information-gathering capabilities of the server. Any software objects utilized pursuant to the column based encoding and query processing can be provided standalone, or distributed across multiple computing devices or objects.

In a network environment in which the communications network/bus 2540 is the Internet, for example, the servers 2510, 2512, etc. can be Web servers with which the clients 2520, 2522, 2524, 2526, 2528, etc. communicate via any of a number of known protocols, such as the hypertext transfer protocol (HTTP). Servers 2510, 2512, etc. may also serve as clients 2520, 2522, 2524, 2526, 2528, etc., as may be characteristic of a distributed computing environment.

Exemplary Computing Device

It should be understood several aspects of the disclosed subject matter may require implementing those aspects via a computing device. Accordingly, the general purpose computer provided in FIG. 26 is provided as an example of such a computing device.

Although not required, embodiments can partly be implemented via an operating system, for use by a developer of services for a device or object, and/or included within application software that operates to perform one or more functional aspects of the various embodiments described herein. Software may be described in the general context of computer-executable instructions, such as program modules, being executed by one or more computers, such as client workstations, servers or other devices. Those skilled in the art will appreciate that computer systems have a variety of configurations and protocols that can be used to communicate data, and thus, no particular configuration or protocol should be considered limiting.

Figure 26:
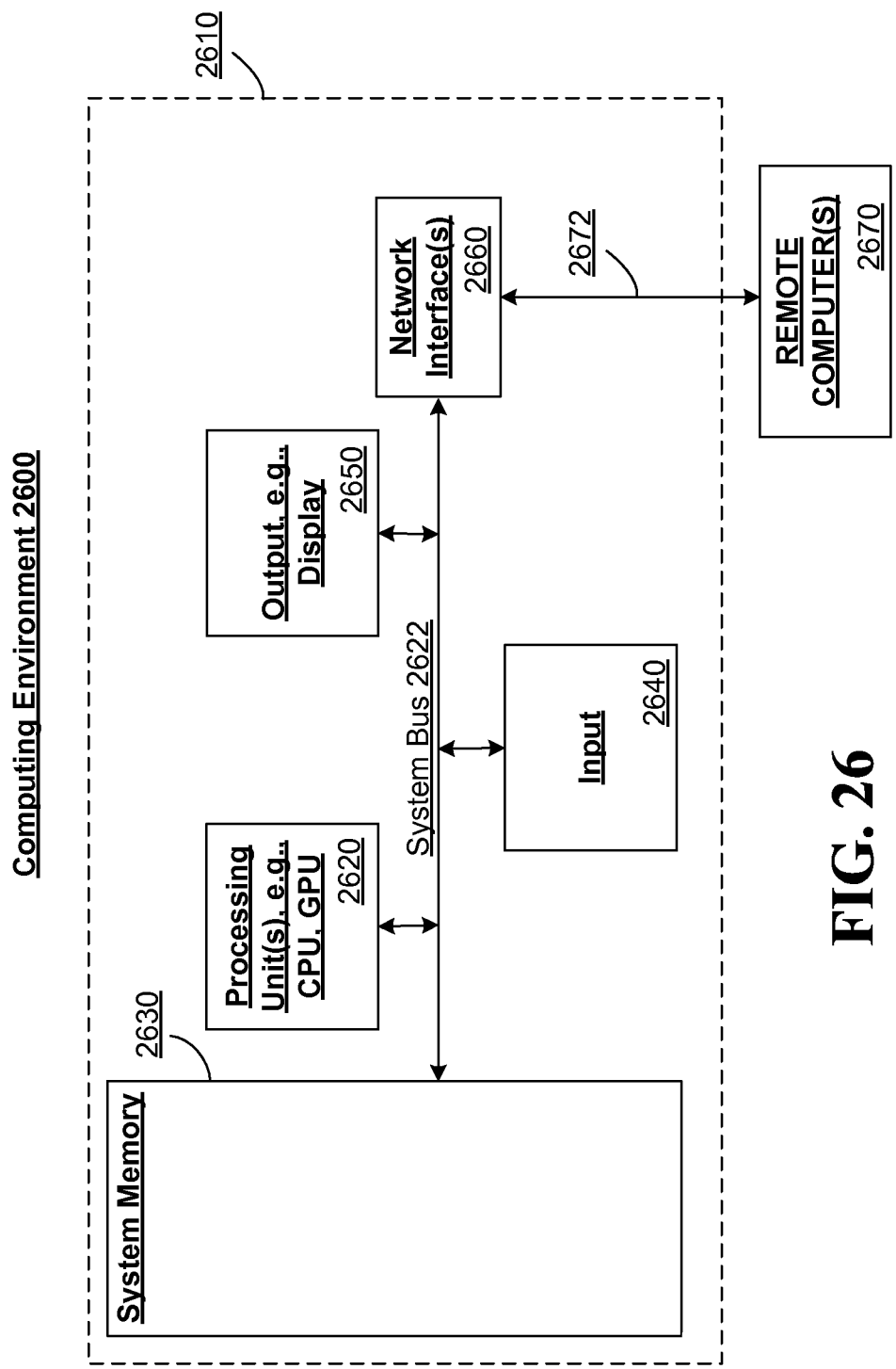
FIG. 26 is a block diagram representing an exemplary non-limiting computing system or operating environment in which one or more aspects of various embodiments described herein can be implemented.

FIG. 26 thus illustrates an example of a suitable computing system environment 2600 in which one or aspects of the embodiments described herein can be implemented, although as made clear above, the computing system environment 2600 is only one example of a suitable computing environment and is not intended to suggest any limitation as to scope of use or functionality. Neither should the computing environment 2600 be interpreted as having any dependency or requirement relating to any one or combination of components illustrated in the exemplary operating environment 2600.

With reference to FIG. 26, an exemplary remote device for implementing one or more embodiments includes a general purpose computing device in the form of a computer 2610. Components of computer 2610 may include, but are not limited to, a processing unit 2620, a system memory 2630, and a system bus 2622 that couples various system components including the system memory to the processing unit 2620.

Computer 2610 typically includes a variety of computer readable media and can be any available media that can be accessed by computer 2610. The system memory 2630 may include computer storage media in the form of volatile and/or nonvolatile memory such as read only memory (ROM) and/or random access memory (RAM). By way of example, and not limitation, memory 2630 may also include an operating system, application programs, other program modules, and program data.

A user can enter commands and information into the computer 2610 through input devices 2640. A monitor or other type of display device is also connected to the system bus 2622 via an interface, such as output interface 2650. In addition to a monitor, computers can also include other peripheral output devices such as speakers and a printer, which may be connected through output interface 2650.

The computer 2610 may operate in a networked or distributed environment using logical connections to one or more other remote computers, such as remote computer 2670. The remote computer 2670 may be a personal computer, a server, a router, a network PC, a peer device or other common network node, or any other remote media consumption or transmission device, and may include any or all of the elements described above relative to the computer 2610. The logical connections depicted in FIG. 26 include a network 2672, such local area network (LAN) or a wide area network (WAN), but may also include other networks/buses. Such networking environments are commonplace in homes, offices, enterprise-wide computer networks, intranets and the Internet.

As mentioned above, while exemplary embodiments have been described in connection with various computing devices and network architectures, the underlying concepts may be applied to any network system and any computing device or system in which it is desirable to compress large scale data or process queries over large scale data.

Also, there are multiple ways to implement the same or similar functionality, e.g., an appropriate API, tool kit, driver code, operating system, control, standalone or downloadable software object, etc. which enables applications and services to use the efficient encoding and querying techniques. Thus, embodiments herein are contemplated from the standpoint of an API (or other software object), as well as from a software or hardware object that provides column based encoding and/or query processing. Thus, various embodiments described herein can have aspects that are wholly in hardware, partly in hardware and partly in software, as well as in software.

The word "exemplary" is used herein to mean serving as an example, instance, or illustration. For the avoidance of doubt, the subject matter disclosed herein is not limited by such examples. In addition, any aspect or design described herein as "exemplary" is not necessarily to be construed as preferred or advantageous over other aspects or designs, nor is it meant to preclude equivalent exemplary structures and techniques known to those of ordinary skill in the art. Furthermore, to the extent that the terms "includes," "has," "contains," and other similar words are used in either the detailed description or the claims, for the avoidance of doubt, such terms are intended to be inclusive in a manner similar to the term "comprising" as an open transition word without precluding any additional or other elements.

As mentioned, the various techniques described herein may be implemented in connection with hardware or software or, where appropriate, with a combination of both. As used herein, the terms "component," "system" and the like are likewise intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on computer and the computer can be a component. One or more components may reside within a process and/or thread of execution and a component may be localized on one computer and/or distributed between two or more computers.

The aforementioned systems have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and that any one or more middle layers, such as a management layer, may be provided to communicatively couple to such sub-components in order to provide integrated functionality. Any components described herein may also interact with one or more other components not specifically described herein but generally known by those of skill in the art.

In view of the exemplary systems described supra, methodologies that may be implemented in accordance with the described subject matter will be better appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Where non-sequential, or branched, flow is illustrated via flowchart, it can be appreciated that various other branches, flow paths, and orders of the blocks, may be implemented which achieve the same or a similar result. Moreover, not all illustrated blocks may be required to implement the methodologies described hereinafter.

In addition to the various embodiments described herein, it is to be understood that other similar embodiments can be used or modifications and additions can be made to the described embodiment(s) for performing the same or equivalent function of the corresponding embodiment(s) without deviating therefrom. Still further, multiple processing chips or multiple devices can share the performance of one or more functions described herein, and similarly, storage can be effected across a plurality of devices. Accordingly, the invention should not be limited to any single embodiment, but rather should be construed in breadth, spirit and scope in accordance with the appended claims.

What is claimed is:

1. A method comprising:
receiving at least one human input via a first receiving component, the at least one human input including data corresponding to a plurality of passive human-brain responses to visualization of a plurality of images;
receiving at least one computer input via a second receiving component, the at least one computer input including data corresponding to a plurality of outputs from a computerized vision-based processing of the plurality of images, said processing of the plurality of images not involving processing passive human-brain responses to visualization of the plurality of images; and
fusing the at least one human input and the at least one computer input with a processor to yield a categorization for at least one of the plurality of images as a function of the at least one human input and the at least one computer input.

2. The method of claim 1, wherein at least one of the plurality of passive human-brain responses is an electroencephalograph (EEG).

3. The method of claim 1, wherein the at least one human input providing similarities between the passive human-brain responses for each of the plurality of images, the at least one computer input providing similarities between the outputs for each of the plurality of images.

4. The method of claim 1, wherein the at least one computer input corresponds to outputs from a pyramid match kernel algorithm.

5. The method of claim 1, wherein the processing comprises processing the at least one human input and the at least one computer input according to a convex kernel algorithm.

6. The method of claim 1, wherein the processing further comprises voting on the categorization for the at least one of the plurality of images.

7. The method of claim 1, further comprising generating a predictive model for categorizing a subsequent set of images.

8. The method of claim 7, wherein the generating of the predictive model comprises generating a distributed computing algorithm for categorizing the subsequent set of images, and wherein at least one of the at least one human input or the at least one computer input includes missing data.

9. The method of claim 7, further comprising selectively sampling the subsequent set of images to improve the accuracy of the predictive model.

10. The method of claim 1, further comprising training a pure computer vision-based system with the at least one human input.

11. A system comprising:
one or more processors; and
memory to maintain a plurality of components executable on the one or more processors, the plurality of components comprising:
a first receiving component to receive at least one human input including data corresponding to a plurality of passive human-brain responses to visualization of a plurality of images;
a second receiving component to receive at least one computer input including data corresponding to a plurality of outputs from a computerized vision-based processing of the plurality of images, said processing of the plurality of images not involving processing passive human-brain responses to visualization of the plurality of images;
a processor coupled to the first and second receiving components and configured to fuse the at least one human input and the at least one computer input to yield a categorization for at least one of the plurality of images as a function of the at least one human input and the at least one computer input.

12. The system of claim 11, wherein the processor is further configured to generate a predictive model for categorizing a subsequent set of images.

13. The system of claim 12, wherein the processor is further configured to implement a Bayesian co-training model.

14. The system of claim 13, wherein the processor is further configured to assign proxy values to missing views.

15. The system of claim 12, wherein the processor is further configured to selectively sample the subsequent images.

16. The system of claim 11, wherein the processor is further configured to process at least one passive human-brain response received as an electroencephalograph (EEG).

17. The system of claim 11, wherein the processor is further configured to process at least one computer input corresponding to outputs from a pyramid match kernel algorithm.

18. The system of claim 11, wherein the processor is further configured to process the at least one human input and the at least one computer input according to a convex kernel algorithm.

19. A method for visual object categorization, the method comprising:
receiving at least one electroencephalograph (EEG) via a first receiving component, the at least one EEG including data corresponding to a plurality of passive human-brain responses to visualization of a plurality of images;
receiving at least one computer input via a second receiving component, the at least one computer input corresponding to outputs from a pyramid match kernel algorithm and including data corresponding to a plurality of outputs from a computerized vision-based processing of the plurality of images, said processing of the plurality of images not involving processing passive human-brain responses to visualization of the plurality of images; and fusing the at least one EEG and the at least one computer input with a processor to generate a categorization for at least one of the plurality of images according to a convex kernel algorithm as a function of the at least EEG and the at least one computer input that are generated using separate processes.

* * * * *